US010711037B2

(12) United States Patent
Cashman

(10) Patent No.: US 10,711,037 B2
(45) Date of Patent: *Jul. 14, 2020

(54) CHEMICAL AND BIOCHEMICAL ADDUCTS AS BIOMARKERS FOR ORGANOPHOSPHATE EXPOSURE

(71) Applicant: Human BioMolucular Research Institute, San Diego, CA (US)

(72) Inventor: John R. Cashman, San Diego, CA (US)

(73) Assignee: Human Biomolecular Research Institute, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/391,614

(22) Filed: Dec. 27, 2016

(65) Prior Publication Data

US 2017/0101441 A1 Apr. 13, 2017

Related U.S. Application Data

(63) Continuation of application No. 12/937,957, filed as application No. PCT/US2009/002342 on Apr. 14, 2009, now Pat. No. 9,549,991.

(60) Provisional application No. 61/124,198, filed on Apr. 14, 2008.

(51) Int. Cl.

| | |
|---|---|
| ***C07K 7/06*** | (2006.01) |
| ***C07K 7/08*** | (2006.01) |
| ***C07K 14/765*** | (2006.01) |
| ***G01N 33/68*** | (2006.01) |
| ***C07K 16/44*** | (2006.01) |
| ***A61K 47/64*** | (2017.01) |
| ***C07K 16/18*** | (2006.01) |
| ***C12P 21/00*** | (2006.01) |

(52) U.S. Cl.

CPC .............. *C07K 7/06* (2013.01); *A61K 47/643* (2017.08); *A61K 47/646* (2017.08); *C07K 7/08* (2013.01); *C07K 14/765* (2013.01); *C07K 16/18* (2013.01); *C07K 16/44* (2013.01); *C12P 21/005* (2013.01); *G01N 33/6842* (2013.01); *G01N 33/6893* (2013.01); *G01N 2333/76* (2013.01); *G01N 2410/00* (2013.01); *G01N 2430/00* (2013.01); *G01N 2430/10* (2013.01); *G01N 2800/42* (2013.01)

(58) Field of Classification Search

CPC . C07K 7/06; C07K 7/08; C07K 14/76; C07K 14/765; C07K 16/44; G01N 33/68; G01N 33/6842; G01N 33/6893; G01N 2333/76; G01N 2333/765; G01N 2410/00; G01N 2430/00; G01N 2430/10; G01N 2800/42; G01N 2800/709

See application file for complete search history.

(56) References Cited

U.S. PATENT DOCUMENTS

| | | | |
|---|---|---|---|
| 4,879,219 A | 11/1989 | Wands et al. | |
| 5,429,941 A | 7/1995 | Lerner et al. | |
| 6,121,004 A | 9/2000 | Pestronk et al. | |
| 9,549,991 B2 * | 1/2017 | Cashman | A61K 47/48284 |
| 2006/0149392 A1 | 7/2006 | Hsieh et al. | |
| 2007/0286846 A1 | 12/2007 | Cashman et al. | |
| 2009/0047307 A1 | 2/2009 | Harrop et al. | |
| 2010/0143342 A1 | 2/2010 | Mudde et al. | |

FOREIGN PATENT DOCUMENTS

| | | | |
|---|---|---|---|
| WO | WO 1993017030 A1 | 9/1993 | |
| WO | WO 2008079185 A2 | 7/2008 | |
| WO | WO-2010039163 A2 * | 4/2010 | G01N 33/6893 |

OTHER PUBLICATIONS

Li et al. "Matrix-assisted laser desorption/ionization . . . assay for organophosphorous toxicants bound to human albumin at Tyr411" Anal. Biochem. (2007) 361: 263-272.

Harlow, E. and Lane, D. "Antibodies: A laboratory manual" Cold Spring Harbor Laboratory 1988, Chapter 4.

Anderson and Taitt, "Water quality monitoring using an automated portable fiber optic biosensor: Raptor" Proc. of SPIE Feb. 2001;4206:1-7.

Anderson et al., "Eight Analyte Detection Using a Four-Channel Optical Biosensor" Sensor Letters 2004:2(1):18-24.

Barzen et al., "Optical multiple-analyte immunosensor far water pollution control" Biosens Bioelectron. Apr. 7, 2002(4): 289-295.

Campbell and McCloskey, "Interferometric Biosensors. Optical Blosensors: Present and Future" Ligler and Taitt., Elsevier 2002: 277-304.

Chen and Mulchandani, "The use of live biocatalysts for pesticide detoxification" Trends Biotechnol. Feb. 16, 1998(2): 71-6.

Delehanty and Ligler, "A Microarray Immunoassay for Simultaneous Detection of Proteins and Bacteria" Anal. Chem. Nov. 1, 2002; 74(21):5681-5687.

Demarco et al., "Rapid Detection of *Escherichia coli* 0157:H7 in Ground Beef Using a Fiber-Optic Biosensor" J. Food Prot. Jul. 1999; 62(7): 711-716.

(Continued)

*Primary Examiner* — Jeffrey E. Russel

(74) *Attorney, Agent, or Firm* — Angelo Castellino

(57) ABSTRACT

Provided are methods for identifying OP-adducted biomarkers of OP exposure as well as compounds containing OPs that can provide OP adducts and compounds of Formula 1 for eliciting antibodies that specifically and selectively bind to the OP adducts, wherein the Formula 1 compounds have the structure of OP-Peptide-Linker-CP, wherein CP is a carrier protein, OP represents a structure corresponding to that of a reactive organic phosphorous compound covalently modifying a tyrosine residue hydroxyl group of the peptide of Formula I and the other variable groups are as described herein.

9 Claims, No Drawings

Specification includes a Sequence Listing.

(56) References Cited

OTHER PUBLICATIONS

Duysen et al., "Evidence for Nonacetylcholinesterase Targets of Organophosphorus Nerve Agent . . . " J. Pharmacol. Exp. Ther. Nov. 2001;299(2) 528-535.
Epstein and Walt, "Fluorescence-based fibre optic arrays: a universal platform for sensing" Chem Soc Rev Jul. 2003; 32(4):203-2.
Feldstein et al., "Array Blosensor: Optical and Fluidics Systems" Biomed. Microdevices 1999;1(2):139-153.
Golden et al., "Portable multichannel fiber optic biosensor for field detection" Opt. Eng. Apr. 1997;36(4):1008-101.
Golden et al., "An automated portable array biosensor" Proc. of SPIE 2003;4968: 27-31. 2003.
Homola et al., "Sulface plasmon resonance biosensors. Optical Biosensors: Present and Future" Ligler and Taitt ,Elsevier 2002: 207-251.
Jbilo et al., "Tissue distribution of human acetylcholinesterase and butyrylcholinesterase messenger RNA" Toxicon Nov. 1994 32(11): 1445-1457.
Jung et al., "RAPTOR: A Fluorimmunoassay-Based Fiber Optic Sensor for Detection of Biological Threats" IEEE Sensors J. Aug. 2003;3(4):352-360.
Kinning and Edwards, "The Resonant Mirror Optical Blosensor. Optical Biosensors: Present and Future" Ligler and Taitt.,Elsevier 2002:253-276.
Kusterbeck, "Flow Immunosensor" Optical Biosensors: Present and Future. 2002: 123-142.
Ligler et al., "Array biosensor for detection of toxins" Anal. Bioanal. Chem Oct. 2003; 377(3):469-477.
Lockridge and Masson, "Pesticides and Susceptible Populations . . . " Neurotoxicology, Feb.-Apr. 2000; 21(1-2);113-126.
Lockridge et al., "Location of Disulfide Bonds within the Sequence of Human Serum Cholinesterase" J. Biol. Chem. Sep. 25, 1987; 262(27): 12945-12952.
Masson et al., "Aging of di-isopropyl-phosphorylated human butyrylcholinesterase" Biochem. J. Oct. 15, 1997;327 (Pt 2): 601-607.
Neville et al., "Aspartate-70 to Glycine Substitution Confers Resistance to . . . In-Ovo Produced Human Butyrylcholinesterase" J. Neurosci. Res. Dec. 1990;27(4):452-460.
Pawlak et al., "Zeptosens' protein microarrays: a novel high performance microarray platform for low abundance protein analysis" Proteomics Apr. 2002;2(4):383-393.
Rosenstock et al., "Chronic central nervous system effects of acute organophosphate pesticide intoxication . . . " Lancet Jul. 27, 1991; 338(8761):223-227.
Rowe et al., "An Array Immunosensor for Simultaneous Detection of Clinical Analytes" Anal. Chem. Jan. 15, 1999;71(2): 433-439.
Rowe, et al., "Array Biosensor for Simultaneous Identification of Bacterial, Viral, and Protein Analytes" Anal. Chem. Sep. 1, 1999 ;71(17):3846-3852.
Sapsford et al., "Kinetics of Antigen Binding to Arrays of Antibodies in Different Sized Spots" Anal. Chem. Nov. 15, 2001;73(22):5518-5524.
Sapsford et al., "Demonstration of Four Immunoassay Formats Using the Array Biosensor" Anal. Chem. Mar. 1, 2002; 74(5):1061-1068.
Sogorb and Vilanova, "Enzymes involved in the detoxification of organophosphorus insecticides through hydrolysis" Toxicol. Lett. Mar. 10, 2002;128(1-3):2.
Taitt et al., "A Portable Array Biosensor for Detecting Multiple Analytes in Complex Samples" Microb. Ecol. Feb. 2004;47(2): 175-185.
Taitt et al., "Detection of *Salmonella enterica* Serovar Typhimurium by Using a Rapid, Array-Based Immunosensor" Appl. Environ. Microbial. Jan. 2004;70(1):152-158.
Wadkins et al., "Patterned Planar Array Immunosensor for Multianalyte Detection" J. Biomed. Optics Jan. 1997; 2(1):74-79.
Xie et al., "Postnatal Developmental Delay and Supersensitivity to Organophosphate in . . . Mice Lacking Acetylcholine esterase" J. Pharmacol. Exp. Ther. Jun. 293(3): 896-902, Jun. 2000.
International Search Report and Written Opinion dated Feb. 7, 2010 issued in PCT/US2009/002342.
Bajgar et al., "Inhibition of blood cholinesterases following intoxication with VX and its derivatives" J. Appl. Toxicol. Sep.-Oct. 2007;27(5):458-463.
Liang et al., "Synthesis of three haptens for the class-specific immunoassay of O,O-dimethyl organophosphorus pesticides . . . " Anal. Chim. Acta. May 19, 2008:815(2):174-183.
Miyoshi et al., "A New Practical Strategy for the Synthesis of Long-Chain Phosphopeptide" Chem. Pharm. Bull. (Tokyo) Aug. 2000;48(8):1230-1233.
Mora et al., "A New Approach to Phosphoserine Phosphothreonine and Phosphotyrosine Synthons.." Int. J. Pept. Protein Res. Jan. 1995;45(1):53-63.
Noort et al., "Verification of Exposure to Organophosphates . . . for Detection of Human Butyrylcholinesterase Adducts" Anal. Chem. Sep. 15, 2006;78(18):6640-6644.
Polhuijs et al., New Method for Retrospective Detection of Exposure to Organophosphorus Anticholinesterases . . . Toxicol. Appl. Pharmacol. Sep. 1997:146(1):156-161.
Holt et al. "Fabrication of a capillary immunosensor in polymethyl methacrylate" Biosens. Bioelectron. Jan. 2002; 17(1-2) 95-103.
Shriver-Lake et al., "Detection of Staphylococcal Enterotoxin B in Spiked Food Samples" J. Food Prot. Oct. 2003; 66 (1 0):1851-1856.

* cited by examiner

SEQUENCE LISTING

<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE
<222> LOCATION: (9)..(9)
<223> OTHER INFORMATION: Xaa = Ser-[P=O(CH3)(O-i-Pr)]

<400> SEQUENCE: 1

Lys Ser Val Thr Leu Phe Gly Glu Xaa Ala Gly Ala Ala
1 5 10

<210> SEQ ID NO 2
<211> LENGTH: 13
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE
<222> LOCATION: (9)..(9)
<223> OTHER INFORMATION: Xaa = Ser-[P=O(CH3)(O-Pinacolyl)]

<400> SEQUENCE: 2

Lys Ser Val Thr Leu Phe Gly Glu Xaa Ala Gly Ala Ala
1 5 10

<210> SEQ ID NO 3
<211> LENGTH: 13
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE
<222> LOCATION: (9)..(9)
<223> OTHER INFORMATION: Xaa = Ser-[P=O(CH3)(O-cyclohexyl)]

<400> SEQUENCE: 3

Lys Ser Val Thr Leu Phe Gly Glu Xaa Ala Gly Ala Ala
1 5 10

<210> SEQ ID NO 4
<211> LENGTH: 13
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE
<222> LOCATION: (9)..(9)
<223> OTHER INFORMATION: Xaa = Ser-[P=O(CH3)(O-Et)]

<400> SEQUENCE: 4

Lys Ser Val Thr Leu Phe Gly Glu Xaa Ala Gly Ala Ala
1 5 10

<210> SEQ ID NO 5
<211> LENGTH: 10
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE -continued

```
<222> LOCATION: (4)..(4)
<223> OTHER INFORMATION: Xaa = Tyr-[P=O(CH3)(O-i-Pr)]

<400> SEQUENCE: 5

Leu Val Arg Xaa Thr Lys Lys Val Pro Gln
1               5                   10


<210> SEQ ID NO 6
<211> LENGTH: 10
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE
<222> LOCATION: (4)..(4)
<223> OTHER INFORMATION: Xaa = Tyr-[P=O(CH3)(O-Pinacolyl)

<400> SEQUENCE: 6

Leu Val Arg Xaa Thr Lys Lys Val Pro Gln
1               5                   10


<210> SEQ ID NO 7
<211> LENGTH: 10
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE
<222> LOCATION: (4)..(4)
<223> OTHER INFORMATION: Xaa = Tyr-[P=O(CH3)(O-cyclohexyl)]

<400> SEQUENCE: 7

Leu Val Arg Xaa Thr Lys Lys Val Pro Gln
1               5                   10


<210> SEQ ID NO 8
<211> LENGTH: 10
<212> TYPE: PRT
<213> ORGANISM: Artificial Sequence
<220> FEATURE:
<223> OTHER INFORMATION: organophosphate modified peptide
<220> FEATURE:
<221> NAME/KEY: MISC_FEATURE
<222> LOCATION: (4)..(4)
<223> OTHER INFORMATION: Xaa = Tyr-[P=O(CH3)(O-Et)]

<400> SEQUENCE: 8

Leu Val Arg Xaa Thr Lys Lys Val Pro Gln
1               5                   10
```

CHEMICAL AND BIOCHEMICAL ADDUCTS AS BIOMARKERS FOR ORGANOPHOSPHATE EXPOSURE

CROSS REFERENCE TO RELATED APPLICATIONS

This application is a continuation of U.S. patent application Ser. No. 12/937,957, now abandoned, which is a national phase application from Intl. Pat. Appl. No. PCT/US2009/002342, filed Apr. 14, 2009, now expired, which claims priority to US provisional Pat. Appl. No. 61/124,198, filed on Apr. 14, 2008.

STATEMENT OF GOVERNMENT RIGHTS

The invention was supported, at least in part, by a grant from the Government of the United States of America (National Institutes of Health (NIH) grant U01 NS058038). The U.S. Government has certain rights to the invention.

SEQUENCE LISTING

Incorporated by reference herein is the ASCII text file having the title of HBRI007US_ST25.txt, created on Dec. 30, 2015, in 2.87 kB providing artificial protein sequences identified by SEQ ID Nos: 1-8.

FIELD

The present invention is in the field of diagnostics, particularly in the area of exposure to organophosphate compounds that inhibit esterases and other enzymes and bind to serum proteins and other proteins, and identification of biomarkers.

BACKGROUND

Recent changes in the security situation facing citizens in the United States and military personnel abroad have greatly increased the threat that chemical weapons will be used against American forces and American civilians in the field as well as at home. Current information indicates that bioterrorists have contemplated using organophosphate (OP) nerve agents. OP nerve gases are a threat to military personnel and civilians (e.g., Gulf War exposure to the military and Tokyo subway system exposure to civilians). In addition, farmers, agricultural workers and pesticide applicators handle large amounts of OPs and are potentially exposed to these toxic materials. Between 150,000 and 300,000 OP-related toxic incidences are reported annually in the United States (Rosenstock, Keifer et al. 1991). This situation points to an urgent need for an efficient, fieldable and inexpensive way to detect OP nerve agents. Available treatment of acute OP nerve agent poisoning only acts in a competitive fashion and is not adequate since it does not prevent neuronal brain damage and incapacitation. Detection instrumentation is an essential component of any protection paradigm, and thus a challenge is to develop decontamination and detection methodology for various OP agents (Chen and Mulchandani 1998; Sogorb and Vilanova 2002).

OP nerve agents act by inhibiting the cholinesterase (ChE) family of enzymes, mostly in the brain, central nervous system and blood. Within the cholinesterase family, acetylcholinesterase (AchE) and butyrylcholinesterase (BchE) are the best known targets. In the case of AchE, the resulting OP adduct inactivates the enzyme, allows acetylcholine (Ach) to build up in the synapse, stimulate autonomic receptors, and block neuromuscular junction receptors. The symptoms resulting from nerve agent exposure are primarily the consequence of accumulation of excess Ach at nerve junctions where ordinarily small amounts of Ach are needed for impulse transmission. Non-cholinergic symptoms have been linked to OP exposure including delayed neuropathy, leukemia, depression, genotoxicity, pulmonary toxicity and vision loss. Evidence for non-AchE targets have been shown with AchE knock-out mice (Xie, Stribley et al. 2000; Duysen, Li et al. 2001).

Other proteins also form adducts with OPs. These proteins include, but are not limited to, serum albumin, transferrin, tubulin, carboxylesterase, acylpeptide hydrolase, fatty acid amide hydrolase, the cannabinoid CB1 receptor, fatty acid synthase, dipeptidyl peptidase 9, prolyl oligopeptidase, long-chain acyl coenzyme A thioesterase, PAF acetylhydrolase 1b, and esterase D/S-formyl glutathione hydrolase, (Tuin et al. Chem Res Toxicol. 2009). The biological effects of adduct formation with these other proteins are not fully understood.

A prominent enzyme for the peripheral hydrolysis of esters (and OP esters) in humans is butyrylcholinesterase (BuChE) also known as serum cholinesterase. BuChE is a glycoprotein of 4 identical subunits (Lockridge et al., 1987). Like the 3D structure of AchE from *Torpedo californica*, the active site of BuChE contains a traditional catalytic triad $Ser^{198}$-$Glu^{325}$-$His^{338}$, and the active site of BuChE is believed to lie near the bottom of a deep and narrow gorge. The enzyme is of toxicological and pharmacological importance and thought to have a role in protection against poisons that are eaten or inhaled (Jbilo et al., 1994; Neville et al., 1990). BuChE scavenges low doses of OP and carbamate pesticides by forming covalent bonds with these agents through the active site serine and therefore protects humans from the toxic effect of these poisons (Lockridge and Masson, 2000). The initial interaction and multi-step subsequent reactions between OPs and ChE is illustrated in Scheme 1 (Masson, Fortier et al. 1997).

When an OP nerve agent reacts with AchE or BuChE, several OP-adducts are possible and the rate of covalent modification (or dealkylation) versus recovery, or aging versus reactivation, plays an important role in the potency and duration of toxicity (in the case of AchE). Most reactive OPs contain a dialkoxy phosphate or phosphonate, and a good leaving group X. The leaving group is generally a halogen, mercaptan (thiolester), phenoxy derivative, or other. The alkoxy phosphonates sarin and soman react with cholinesterase to afford phosphono-cholinesterase adducts after loss of $F^-$. Likewise, VX forms a phosphono-cholinesterase adduct. Some OP-modified cholinesterases are prone to non-reactivation, aging or other post-inhibitory mechanisms. This is important in certain nerve gas exposures in that "aging" is a determinant endpoint of the cholinesterase inhibition mechanism.

OP insecticides resemble OP nerve agents closely, except that they usually have a P═S bond instead of a P═O bond. OP insecticides generally require oxidative desulfuration to the P═O compound to exhibit maximum toxicity, but thereafter the chemical interaction with AchE is the same. It is known that replacing the P═O moiety with P═S generally reduces the reactivity of the OP (although biological oxidation to the P═O compound restores reactivity). When potentially reactive ethoxy or methoxy groups are replaced with their corresponding alkyl analogs (i.e., propyl or ethyl, respectively), the potential toxicity of the resulting compounds also decreases. Thus, the phosphonylated serine residues of AchE and BuChE are highly information rich molecules and indicate the type and amount of OP exposure whether it is from a nerve agent or a pesticide. A method of detection that may identify the precise OP agent (or agents) and exposure so that appropriate treatment and response can be taken is needed.

Human serum albumin (hSA) makes up 50-60% of serum proteins. hSA possesses an esterase and amidase activity. It has also been shown that hSA has the ability to bind OP agents. Binding of OPs to hSA occurs at tyrosine 411. Such a property makes hSA a potential biomarker for detection of exposure to OP reagents.

Antibodies elicited against the OP adducts of ChE members and against hSA or other enzymes or binding proteins may be used to determine an exposure to OP. Individual OPs form adducts specific to that reagent. Therefore, antibodies against each OP-adducted protein provide important information in determining exposure to a particular OP. This knowledge can lead to faster treatment and fewer long-term adverse health effects.

SUMMARY

In one embodiment, disclosed are compounds of the following Formula I

OP-Peptide-Linker-CP (I), and salts thereof,
wherein:
OP is

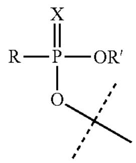

selected from the group consisting of reactive organophosphorus reagents, nerve agents and pesticides; the stereochemistry at phosphorus may be $S_p$ and $R_p$ stereoisomers, or a mixture of $S_p$ and $R_p$ stereoisomers;

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' is selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino;

Peptide is a sequence of amino acids containing serine, threonine or tyrosine to which an OP is attached;

Linker is an amino acid or other bifunctional group capable of covalently linking OP-Peptide to the CP; and CP is a conjugate protein used to display haptens for antibody generation. In one embodiment CP is Keyhole Limpet Hemocyanin (KLH).

In one embodiment, Peptide is a sequence of amino acids containing serine, threonine or tyrosine derived from proteins modified by an OP nerve agent.

In another embodiment, Peptide is a sequence of amino acids containing serine, threonine or tyrosine derived from proteins modified by a pesticide. In one embodiment, Peptide mimics the active site of AChE or BuChE. In another embodiment, Peptide mimics the active site of serine or threonine containing protein to which an OP binds. In one embodiment, Peptide is a sequence of amino acids containing a tyrosine to which an OP is attached. In another embodiment, Peptide mimics the region around tyrosine 411 of human serum albumin. In yet another embodiment, Peptide mimics the active site of a tyrosine containing protein where an OP binds. In one embodiment, the total number of amino acids constituting Peptide is between 7 and 41. In one embodiment, the linker is aminocaproic acid. In another embodiment, the linker is cysteine. In another embodiment, CP is Bovine Serum Albumin (BSA).

In another embodiment, disclosed are compounds of the following Formula (II):

OP-Peptide-Linker (II)

and salts thereof,
wherein:
OP is

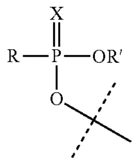

selected from the group consisting of reactive organophosphorus reagents, nerve agents and pesticides; the stereochemistry at phosphorus may be $S_p$ and $R_p$ stereoisomers, or a mixture of $S_p$ and $R_p$ stereoisomers;

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' is selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino;

Peptide is a sequence of amino acids containing serine, threonine or tyrosine to which an OP is attached; and Linker is an amino acid or other bifunctional group capable of covalently linking OP-peptide to the CP. In one embodiment, the linker is aminocaproic acid. In another embodiment, the linker is cysteine.

In one embodiment, Peptide is a sequence of amino acids containing serine, threonine or tyrosine derived from proteins modified by an OP nerve agent. In another embodiment, Peptide is a sequence of amino acids containing serine, threonine or tyrosine derived from proteins modified by a pesticide. In one embodiment, the total number of amino acids constituting Peptide is between 7 and 41.

In yet another embodiment, provided are compounds of the following Formula III:

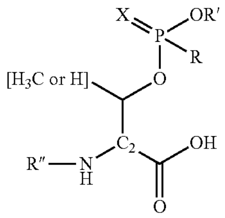

(III)

and salts thereof, wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

R" is a nitrogen protecting group. In one embodiment, R" is Fmoc;

X is oxygen, sulfur, selenium or imino;

the stereochemistry at $C_2$ may be R or S; and the stereochemistry at the phosphorus atom may be $S_p$ and $R_p$ stereoisomers, or a mixture of $S_p$ and $R_p$ stereoisomers.

In another embodiment, provided are compounds of the following Formula (IV):

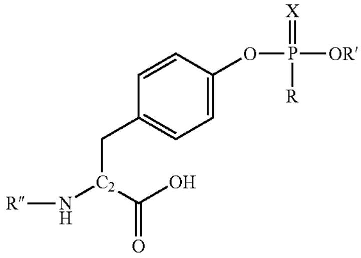

(IV)

and salts thereof, wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, or cyclohexyl;

R" is a nitrogen protecting group. In one embodiment, R" is Fmoc;

X is oxygen, sulfur, selenium or imino;

the stereochemistry at $C_2$ may be R or S; and the stereochemistry at the phosphorus atom may be $S_p$ and $R_p$ stereoisomers, or a mixture of $S_p$ and $R_p$ stereoisomers.

In one embodiment, provided are methods for preparation of the compounds of Formula (III). In another embodiment, provided are methods for preparation of the compounds of Formula (IV).

In one embodiment, provided are methods of using the compounds of Formula (III) or Formula (IV) to synthesize the compounds of Formula (II). In one embodiment, the compounds of Formula (II) consist of peptides bearing an OP adduct and a linker.

In one embodiment, provided are methods of using the compounds of Formula (III) or Formula (IV) to synthesize the compounds of Formula (I). In one embodiment, the compounds of Formula (I) consist of peptides bearing an OP adduct and a linker conjugated to a CP protein.

In one embodiment, provided are methods for using the compounds of Formula (I) to generate monoclonal or polyclonal antibodies specific for an OP-peptide.

In one embodiment, provided are methods for using antibodies against the compounds of Formula (I) to diagnose the presence, identity and quantity of OP adducts in biological fluids in order to determine exposure to nerve agents, pesticides, or other active OP agents known to covalently modify proteins.

In one embodiment, provided are compounds of the following Formula (V) containing a thiocholine moiety:

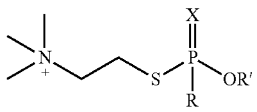

(V)

and salts thereof, wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino; and the stereocenter at the phosphorus atom may be $S_p$ and $R_p$ stereoisomers, or a mixture of $S_p$ and $R_p$ stereoisomers.

In one embodiment, provided are compounds of the following Formula (VI) containing a dimethylaminoethylthio moiety:

(VI)

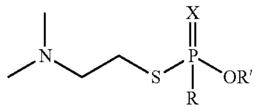

and salts thereof, wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino; and the stereocenter at the phosphorus atom may be $S_p$ and $R_p$ stereoisomers, or a mixture of $S_p$ and $R_p$ stereoisomers.

In one embodiment, provided are methods for preparation of the compounds of Formula (V). In another embodiments, provided are methods for preparation of the compounds of Formula (VI).

In one embodiment, provided are methods of using the compounds of Formula (V) for the identification of modified sites in target proteins. In another embodiment, provided are methods of using the compounds of Formula (VI) for the identification of modified sites in target proteins.

DETAILED DESCRIPTION

In one embodiment, provided is a chemical biology strategy for identification of chemical adducts that are formed when humans or small animals come into contact with OP reagents. Described herein are phosphonylated serine and tyrosine adducts that imitate the adducts of serine and tyrosine when they are in contact with OP reagents. While not limiting, the technology is also applicable to phosphorylated adducts. These compounds are used in the construction of the compounds of Formulae I and II.

Definitions

The term OP refers to reactive organophosphorus reagent. The term OP-adduct refers to the covalent product formed when an amino acid or a peptide or a protein are treated with or mixed with an OP reagent. The term conjugate refers to the product of attaching the peptide to the carrier protein.

One diastereomer or enantiomer of a compound disclosed herein may display superior biological activity compared with the other. When required, separation of the diastereomers or enantiomers can be achieved by using a chiral auxiliary attached to the phosphorus center, separation by chromatographic methods, followed by removal of the auxiliary. Alternatively, the diastereomers or enantiomers may be separated by chromatography using a chiral stationary phase. While not specifying the chirality of the molecule, the technology is applicable to centers of chirality with either stereochemistry.

Specific values listed below for radicals, substituents, and ranges are for illustration only, they do not exclude other defined values or other values within defined ranges for the radicals and substituents.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxy. When a substituent is keto (i.e., =O) or thioxo (i.e., =S) group, then 2 hydrogens on the atom are replaced.

"Alkyl" refers to a $C_1$-$C_{18}$ hydrocarbon containing normal, secondary, tertiary or cyclic carbon atoms. Examples are methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$.

The alkyl can optionally be substituted with one or more alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl. The alkyl can optionally be interrupted with one or more non-peroxide oxy (—O—), thio (—S—), carbonyl (—C(═O)—), carboxy (—C(═O)O—), sulfonyl (SO) or sulfoxide ($SO_2$). Additionally, the alkyl can optionally be at least partially unsaturated, thereby providing an alkenyl.

"Alkenyl" refers to a C2-C18 hydrocarbon containing normal, secondary, tertiary or cyclic carbon atoms with at least one site of unsaturation, i.e., a carbon-carbon, spa double bond. Examples include, but are not limited to: ethylene or vinyl ($—CH═CH_2$), allyl ($—CH_2CH═CH_2$), cyclopentenyl ($—C_5H_7$), and 5-hexenyl ($—CH_2CH_2CH_2CH_2CH═CH_2$).

The alkenyl can optionally be substituted with one or more alkyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl. Additionally, the alkenyl can optionally be interrupted with one or more peroxide oxy (—O—), thio (—S—), carbonyl (—C(═O)—), carboxy (—C(═O)O—), sulfonyl (SO) or sulfoxide ($SO_2$).

"Alkylidenyl" refers to a $C_1$-$C_{18}$ hydrocarbon containing normal, secondary, tertiary or cyclic carbon atoms. Examples are methylidenyl ($═CH_2$), ethylidenyl ($═CHCH_3$), 1-propylidenyl ($═CHCH_2CH_3$), 2-propylidenyl ($═C(CH_3)_2$), 1-butylidenyl ($═CHCH_2CH_2CH_3$), 2-methyl-1-propylidenyl ($═CHCH(CH_3)_2$), 2-butylidenyl ($═C(CH_3)CH_2CH_3$), 1-pentyl ($═CHCH_2CH_2CH_2CH_3$), 2-pentylidenyl ($═C(CH_3)CH_2CH_2CH_3$), 3-pentylidenyl ($═C(CH_2CH_3)_2$), 3-methyl-2-butylidenyl ($═C(CH_3)CH(CH_3)_2$), 3-methyl-1-butylidenyl ($═CHCH_2CH(CH_3)_2$), 2-methyl-1-butylidenyl ($═CHCH(CH_3)CH_2CH_3$), 1-hexylidenyl ($═CHCH_2CH_2CH_2CH_2CH_3$), 2-hexylidenyl ($═C(CH_3)CH_2CH_2CH_2CH_3$), 3-hexylidenyl ($═C(CH_2CH_3)(CH_2CH_2CH_3)$), 3-methyl-2-pentylidenyl ($═C(CH_3)CH(CH_3)CH_2CH_3$), 4-methyl-2-pentylidenyl ($═C(CH_3)CH_2CH(CH_3)_2$), 2-methyl-3-pentylidenyl ($═C(CH_2CH_3)CH(CH_3)_2$), and 3,3-dimethyl-2-butylidenyl ($═C(CH_3)C(CH_3)_3$.

The alkylidenyl can optionally be substituted with one or more alkyl, alkenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl. Additionally, the alkylidenyl can optionally be interrupted with one or more non-peroxide oxy (—O—), thio (—S—), carbonyl (—C(═O)—), carboxy (—C(═O)O—), sulfonyl (SO) or sulfoxide ($SO_2$).

"Alkenylidenyl" refers to a $C_2$-$C_2$ hydrocarbon containing normal, secondary, tertiary or cyclic carbon atoms with at least one site of unsaturation, i.e., a carbon-carbon, spa double bond. Examples include, but are not limited to: allylidenyl ($═CHCH═CH_2$), and 5-hexenylidenyl ($═CHCH_2CH_2CH_2CH═CH_2$).

The alkenylidenyl can optionally be substituted with one or more alkyl, alkenyl, alkylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl. Additionally, the alkenylidenyl can optionally be interrupted with one or more non-peroxide oxy (—O—), thio (—S—), carbonyl (—C(═O)—), carboxy (—C(═O)O—), sulfonyl (SO) or sulfoxide ($SO_2$).

"Alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene ($—CH_2—$), 1,2-ethyl ($—CH_2CH_2—$), 1,3-propyl ($—CH_2CH_2CH_2—$), 1,4-butyl ($—CH_2CH_2CH_2CH_2—$), and the like.

The alkylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl. Additionally, the alkylene can optionally be interrupted with one or more nonperoxide oxy (—O—), thio (—S—), carbonyl (—C(═O)—), carboxy (—C(═O)O—), sulfonyl (SO) or sulfoxide ($SO_2$). Moreover, the alkylene can optionally be at least partially unsaturated, thereby providing an alkenylene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

The alkenylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_x$, wherein each $R_x$ and $R_y$ are independently H, alkyl, alkenyl, aryl, heteroaryl, heterocycle, cycloalkyl or hydroxyl. Additionally, The alkenylene can optionally be interrupted with one or more non-peroxide oxy (—O—), thio (—S—), carbonyl (—C(═O)—), carboxy (—C(═O)O—), sulfonyl (SO) or sulfoxide ($SO_2$).

The term "alkynyl" refers to unsaturated groups which contain at least one carbon-carbon triple bond and includes straight chain, branched chain, and cyclic groups, all of which may be optionally substituted. Suitable alkynyl groups include ethynyl, propynyl, butynyl and the like which may be optionally substituted.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more alkyl, alkylidenyl, alkenylidenyl, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkenyl, alkoxy, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl.

The cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4Hquinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl.

The term "heterocycle" refers to a saturated or partially unsaturated ring system, containing at least one heteroatom selected from the group oxygen, nitrogen, and sulfur, and optionally substituted with alkyl or $C(=O)OR_b$, wherein $R_b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The heterocycle can optionally be substituted with one or more alkyl, alkenyl, alkoxy, halo, haloalkyl, hydroxy, hydroxyalkyl, aryl, heteroaryl, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_x$, wherein each $R_x$ and $R_y$ are independently H, alkyl, aryl, heteroaryl, heterocycle, cycloalkyl or hydroxyl.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. In one specific embodiment of the invention, the nitrogen heterocycle can be 3-methyl-5,6-dihydro-4H-pyrazino[3,2,1-jk]carbazol-3-ium iodide.

Another class of heterocyclics is known as "crown compounds" which refers to a specific class of heterocyclic compounds having one or more repeating units of the formula $[-(CH_2-)_aA-]$ where a is equal to or greater than 2, and A at each separate occurrence can be O, N, S or P. Examples of crown compounds include, by way of example only, $[-(CH_2)_3-NH-]_3$, $[-((CH_2)_2-O)_4-((CH_2)_2-NH)_2]$ and the like. Typically such crown compounds can have from 4 to 10 heteroatoms and 8 to 40 carbon atoms.

The term "alkanoyl" refers to C(=O)R, wherein R is an alkyl group as previously defined.

The term "acyloxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to C(=O)OR, wherein R is an alkyl group as previously defined.

The term "amino" refers to —$NH_2$, and the term "alkylamino" refers to —$NR_2$, wherein at least one R is alkyl and the second R is alkyl or hydrogen. The term "acylamino" refers to RC(=O)N, wherein R is alkyl alkylidenyl, aryl, heteroaryl and the like.

The term "imino" refers to —C=N—[H or C—].

The term "nitro" refers to —$NO_2$.

The term "trifluoromethyl" refers to —$CF_3$.

The term "trifluoromethoxy" refers to —$OCF_3$.

The term "cyano" refers to —CN.

The term "hydroxy" or "hydroxyl" refers to —OH.

The term "oxy" refers to —O—.

The term "thio" refers to —S—.

The term "thioxo" refers to (=S).

The term "keto" refers to (=O).

The term "thiophosphoro" refers to (P=S).

As used herein, "nucleic acid base" refers to a nitrogenous base that is planar, aromatic and heterocyclic. They are typically derivatives of either purine or pyrimidine. Suitable nucleic acid bases include, e.g., purine, pyrimidine, adenine, guanine, cytosine, uracil, and thymine.

The nucleic acid base can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and/or $COOR_x$, wherein each $R_x$ and $R_y$ are independently H, alkyl, alkenyl, aryl, heteroaryl, heterocycle, cycloalkyl or hydroxy.

As used herein, "amino acid" refers to a compound with an amine and a carboxylic acid separated by a CHR or $CH_2CHR$ as in beta-amino acids. The R descriptor refers to the side chain in the amino acid.

The amino acid side chain R may be any of the naturally occurring amino acids in nature or any of the unnatural amino acids such as ornithine. Examples of Amino acid side chain R groups include, but are not limited to, H (Glycine), $CH_3$ (Alanine), $CH_2OH$ (Serine), $CH_2$-Phenyl (Phenylalanine) and the like. Other amino acid side chains are known to one skilled in the art.

The amino acid stereocenter may be R or S.

As used herein, the term "peptide" refers to a sequence of natural or unnatural amino acids covalently linked together via amide bonds. Methods for making peptides from amino acids are known in the art and are incorporated herein by reference. A peptide contains a minimum of two amino acids, with a maximum of 100 amino acids, preferably 7 to 41 amino acids. Some peptides are capable of forming adducts with OPs. These peptides include, but are not limited to, serum albumin, transferrin, tubulin, carboxylesterase, acylpeptide hydrolase, fatty acid amide hydrolase, the cannabinoid CB1 receptor, fatty acid synthase, dipeptidyl peptidase 9, prolyl oligopeptidase, long-chain acyl coenzyme A thioesterase, PAF acetylhydrolase 1b, and esterase D/S-formyl glutathione hydrolase, As used herein, the term "linker" refers to a bifunctional reagent, containing e.g. a carboxyl group and an amine group, or a thiol group, separated by a variable number of atoms; the linker may be used to covalently attach the peptide to a larger protein, resin, or solid support. Preferred linkers are beta alanine, aminopropanoic acid, aminobutyric acid, aminopentanoic acid, aminocaproic acid, cysteine, homocysteine, and the like.

As used herein, the term "conjugate protein" refers to a protein to which a hapten is covalently attached for the purpose of eliciting an immune response to the hapten. Examples of conjugate proteins include, but are not limited to, KLH (keyhole limpet hemocyanin) and BSA (bovine serum albumin), and the like.

As used herein, the term "salt" refers to a complex formed between a charged molecule and a suitable counterion to form a neutral species. Example of salts for positively charged compounds include but are not limited to fluoride, chloride, bromide, iodide, acetate, sulfate, nitrate, citrate, bicarbonate and the like. Examples of salts for negatively charged compounds include, but are not limited to sodium, potassium, cesium, calcium, magnesium, and the like.

The term "protecting group" refers to a chemical functionality designed to temporarily block a portion of a molecule from chemical modification during synthetic steps. An extensive list of such protecting groups can be found in "Protective Groups in Organic Synthesis", 4th Edition, 2006, by Theodora W. Greene & Peter G. M. Wuts. Examples of protecting groups for nitrogen in amino acids include, but are not limited to, carbamates, substituted ethyl carbamates, miscellaneous carbamates, urea-type derivatives, amides, cyclic imide derivatives, N-alkyl amines, N-aryl amines, imine derivatives, enamine derivatives, N-hetero atom derivatives, assisted cleavage or photolytic cleavage. Examples of carbamates include, but are not limited to, methyl, ethyl, 9-fluorenylmethyl, 9-(2-sulfo) fluorenylmethyl, 9-(2,7-dibromo)fluorenylmethyl, 17-tetrabenzo[a, c, g, i] fluorenylmethyl, 2-chloro-3-indenylmethyl, benz[f]inden-3-ylmethyl, 2,7-di-t-butyl [9-(10,10-dioxo-10, 10,10,10-tetrahydrothioxanthyl)methyl, and 1,1-dioxobenzo [b]thiophene-2-ylmethyl. Examples of substituted ethyl carbamates include, but are not limited to, 2,2,2,-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-(3,5-di-t-butylphenyl)-1-methylethyl, 1-methyl-1-(4-biphenyl)ethyl, t-butyl, 1-adamantyl, vinyl, allyl, cinnamyl, 1-isopropylallyl, 4-nitrocinnamyl, 3-(3'-pyridyl) prop-2-enyl, 8-quinolyl, N-hydroxypiperidinyl, alkyldithio, and benzyl. Examples of urea-type derivatives include, but not limited to, phenothiazinyl-(10)-carbonyl, N'-p-toluenesulfonylaminocarbonyl, and N'-phenylaminothiocarbonyl. Also nitrogen protecting groups include, but not limited to, t-butyl-oxycarbonyl (Boc), fluorenylmethyl-oxycarbonyl (Fmoc), and benzyloxycarbonyl (Cbz).

As to any of the above groups, which contain one or more substituents, it is understood that such groups do not contain any substitution or substitution patterns which are sterically impractical and/or synthetically non-feasible. In addition, the compounds of this invention include all stereochemical isomers arising from the substitution of these compounds.

Obviously, numerous modifications and variations of the present invention are possible in light of the above teachings. It is therefore to be understood that within the scope of the appended claims, the invention may be practiced otherwise than as specifically described herein.

Compounds

In one embodiment, disclosed are compounds of the following Formula I:

OP-Peptide-Linker-CP (I), wherein:

OP is

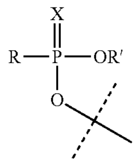

selected from the group consisting of reactive organophosphorus reagents, nerve agents and pesticides; the stereochemistry at phosphorus may be $S_p$ and $R_p$ stereoisomers, or a mixture of $S_p$ and $R_p$ stereoisomers;

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' is selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino;

Peptide is a sequence of amino acids containing serine, threonine or tyrosine to which an OP is attached;

Linker is an amino acid or other bifunctional reagent capable of covalently linking OP-peptide to the CP. In one embodiment, the linker is aminocaproic acid. In another embodiment, the linker is cysteine;

CP is a conjugate protein used to display haptens for antibody generation. In one embodiment CP is KLH (Keyhole Limpet Hemocyanin);

and salts thereof.

In one embodiment, a peptide is a sequence of amino acids containing serine, threonine or tyrosine derived from proteins modified by an OP nerve agent. In another embodiment, a peptide is a sequence of amino acids containing serine, threonine or tyrosine derived from proteins modified by a pesticide. In one embodiment, a sequence mimics the active site of AChE or BuChE. In another embodiment, a sequence mimics the active site of serine or threonine containing protein to which an OP is known to bind. In one embodiment, a peptide is a sequence of amino acids containing a tyrosine to which an OP is attached. In another embodiment, the sequence mimics the region around tyrosine 411 of human serum albumin. In yet another embodiment, the sequence mimics the active cite of a tyrosine containing protein where an OP is known to bind. In one embodiment, the total number of amino acids constituting peptide is between 7 and 41. In another embodiment, CP is BSA (Bovine Serum Albumin).

In another embodiment, disclosed are compounds of the following Formula (II):

OP-Peptide-Linker (II)

wherein:

OP is

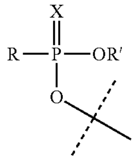

selected from the group consisting of reactive organophosphorus reagents, nerve agents and pesticides; the stereochemistry at phosphorus may be $S_p$ and $R_p$ stereoisomers, or a mixture of $S_p$ and $R_p$ stereoisomers;

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' is selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino;

Peptide is a sequence of amino acids containing serine, threonine or tyrosine to which an OP is attached;

Linker is an amino acid or other bifunctional reagent capable of covalently linking OP-peptide to the CP;

and salts thereof.

In one embodiment, the linker is aminocaproic acid.

In one embodiment, a peptide is a sequence of amino acids containing serine, threonine or tyrosine derived from proteins modified by an OP nerve agent. In another embodiment, a peptide is a sequence of amino acids containing serine, threonine or tyrosine derived from proteins modified by a pesticide. In one embodiment, the total number of amino acids constituting peptide is between 7 and 41. In another embodiment, the linker is cysteine; and salts thereof.

In yet another embodiment, provided are compounds of the following Formula III:

(III)

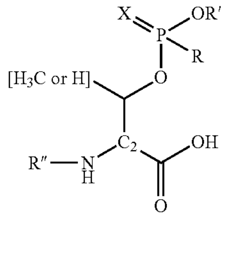

wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

R" is Fmoc, Boc, Cbz or some other suitable blocking group;

X is oxygen, sulfur, selenium or imino;

the stereochemistry at $C_2$ may be R or S;

the stereochemistry at the phosphorus atom may be $S_p$ and $R_p$ stereoisomers, or a mixture of $S_p$ and $R_p$ stereoisomers; and salts thereof.

In another embodiment, provided are compounds of the following Formula (IV):

(IV)

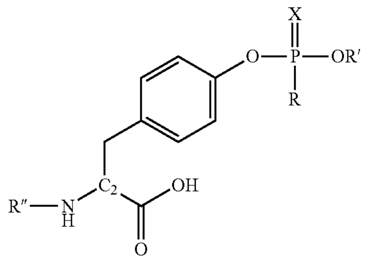

wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, or cyclohexyl;

R" is Fmoc, Boc, Cbz or some other suitable blocking group;

X is oxygen, sulfur, selenium or imino;

the stereochemistry at $C_2$ may be R or S;

the stereochemistry at the phosphorus atom may be $S_p$ and $R_p$ stereoisomers, or a mixture of $S_p$ and $R_p$ stereoisomers; and salts thereof.

In one embodiment, provided are methods for preparation of the compounds of Formula (III). In another embodiment, provided are methods for preparation of the compounds of Formula (IV).

In one embodiment, provided are methods of using the compounds of Formula (III) or Formula (IV) to synthesize the compounds of Formula (II). In one embodiment, the compounds of Formula (II) consist of peptides bearing an OP adduct and the Linker.

In one embodiment, provided are methods of using the compounds of Formula (III) or Formula (IV) to synthesize the compounds of Formula (I). In one embodiment, the compounds of Formula (I) consist of peptides bearing an OP adduct and the linker conjugated to a CP protein.

In one embodiment, provided are compounds of the following Formula (V) containing a thiocholine moiety:

(V)

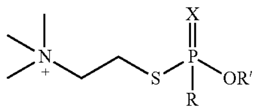

wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino;

the stereocenter at the phosphorus atom may be $S_p$ and $R_p$ stereoisomers, or a mixture of $S_p$ and $R_p$ stereoisomers; and salts thereof.

In one embodiment, provided are methods for preparation of the compounds of Formula (V). In one embodiment, provided are methods of using the compounds of Formula (V) for the identification of modified sites in target proteins.

In one embodiment, provided are compounds of the following Formula (VI) containing a dimethylaminoethylthio moiety:

(VI)

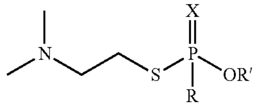

wherein:

R is alkyl, substituted alkyl, alkenyl, substituted alkenyl, alkynyl, substituted alkynyl, alkylidenyl, substituted alkylidenyl, alkenylidenyl, substituted alkenylidenyl, alkoxy, substituted alkoxy, halo, haloalkyl, hydroxy, hydroxyalkyl, aryl, substituted aryl, heteroaryl, substituted heteroaryl, heterocycle, substituted heterocycle, cycloalkyl, substituted cycloalkyl, amino, substituted amino, alkylamino, acylamino, trifluoromethyl, trifluoromethoxy, cyano, methyl, ethyl, isopropyl, n-propyl, n-butyl, tert-butyl, cyclohexyl, pinacolyl, methoxy, ethoxy, propoxy, or dimethylamino;

R' selected from the group consisting of alkyl, substituted alkyl, alkenyl, substituted alkenyl, alkynyl, substituted alkynyl, alkylidenyl, substituted alkylidenyl, alkenylidenyl, substituted alkenylidenyl, haloalkyl, hydroxyalkyl, aryl, substituted aryl, heteroaryl, substituted heteroaryl, heterocycle, substituted heterocycle, cycloalkyl, substituted cycloalkyl, trifluoromethyl, methyl, ethyl, isopropyl, pinacolyl, and cyclohexyl;

X is oxygen, sulfur, selenium or imino;

the stereocenter at the phosphorus atom may be $S_p$ and $R_p$ stereoisomers, or a mixture of $S_p$ and $R_p$ stereoisomers;

and salts thereof.

In another embodiment, provided are methods for preparation of the compounds of Formula (VI). In another embodiment, provided are methods of using the compounds of Formula (VI) for the identification of modified sites in target proteins.

The compounds provided herein can be synthesized using well-known synthetic organic chemistry techniques. Schemes 1 through 4 below show synthetic pathways that are used in synthesizing some of the compounds disclosed herein. Those skilled in the art will recognize that these examples are meant to illustrate and not limit the present disclosure.

Scheme 1: Synthesis of serine and threonine phosphonate reagents

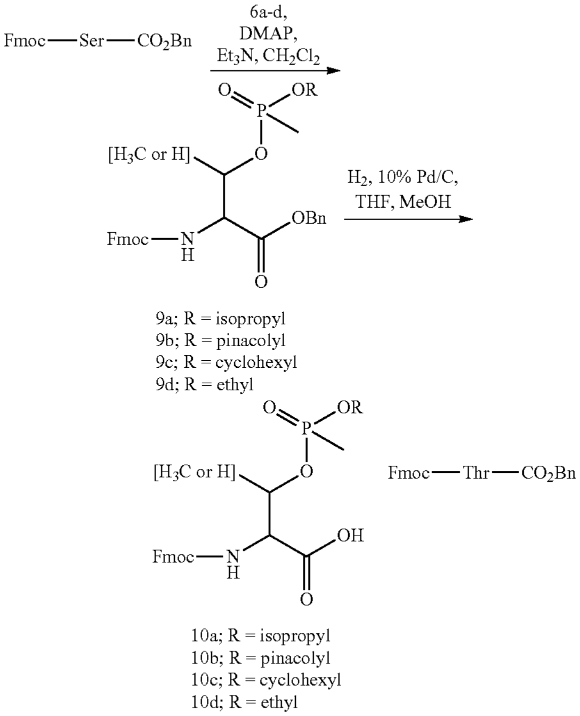

Scheme 2: Synthesis of tyrosine phosphonate reagents

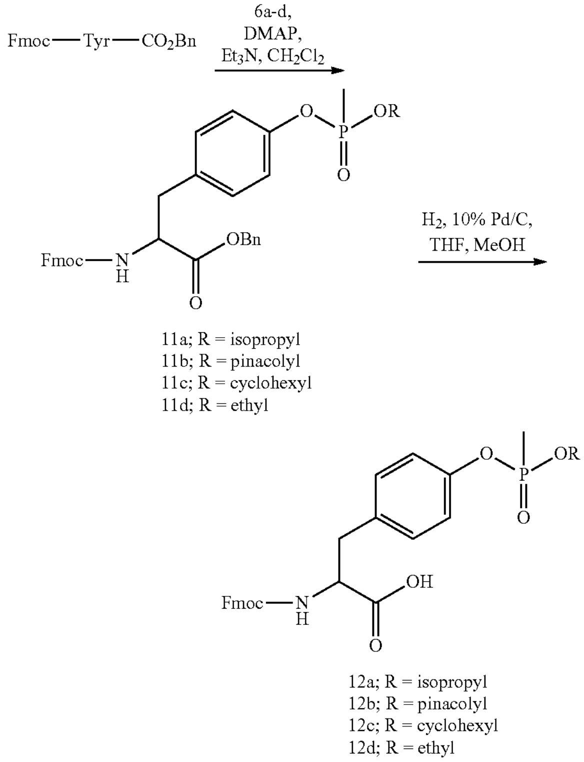

Scheme 3: Chemical synthesis of enantiomerically enriched $S_p$ nerve agent analogs for GB, GF and GD (18-$S_p$ to 23-$S_p$).

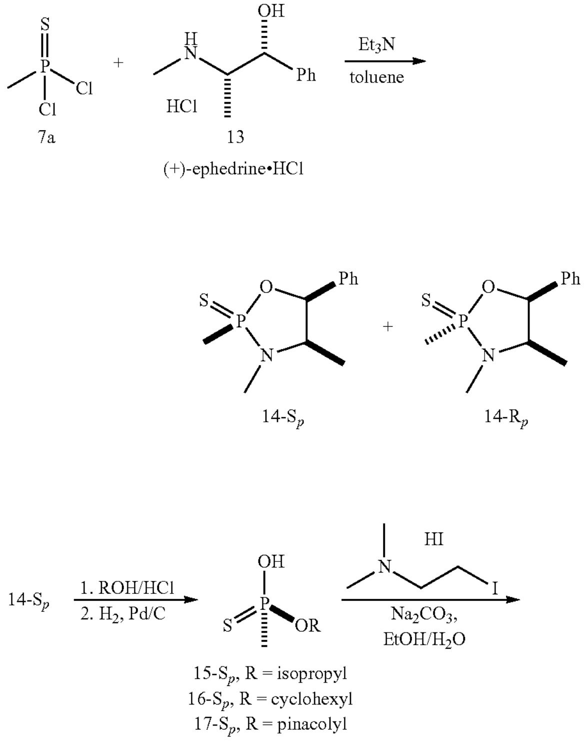

-continued

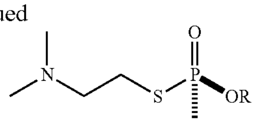

18-$S_p$, R = isopropyl
19-$S_p$, R = cyclohexyl
20-$S_p$, R = pinacolyl

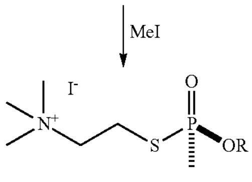

21-$S_p$, R = isopropyl
22-$S_p$, R = cyclohexyl
23-$S_p$, R = pinacolyl

The synthesis of $R_p$ nerve agent analogs follows the same scheme using intermediate 14-$R_p$ (scheme not shown).

Scheme 4: Chemical synthesis of enantiomerically enriched $S_p$ nerve agent analogs for GA (27-$S_p$ and 28-$S_p$).

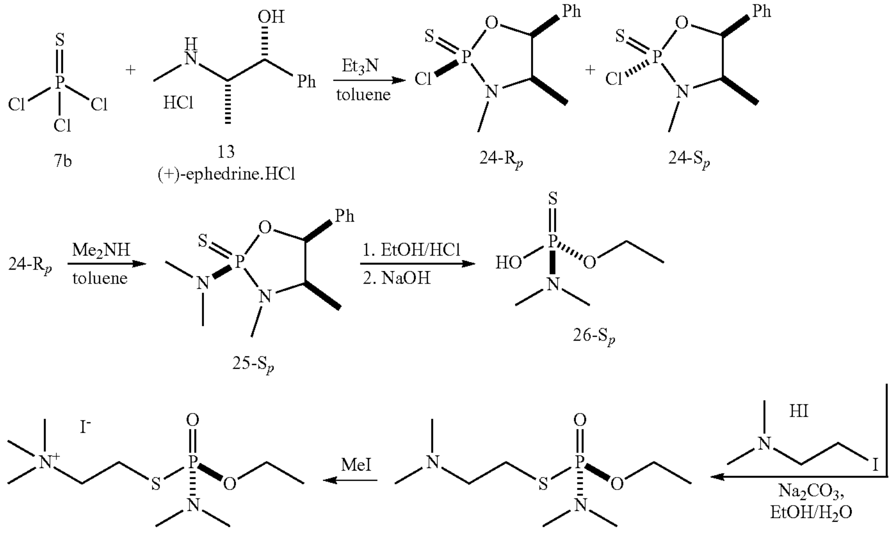

7b
13
(+)-ephedrine.HCl
24-$R_p$
24-$S_p$
25-$S_p$
26-$S_p$
27-$S_p$
28-$S_p$

The synthesis of $R_p$ nerve agent analogs follows the same scheme using intermediate 24-$S_p$ (scheme not shown).

The compounds of structures 8 and 12 are incorporated into peptides of sequences surrounding the reactive serine in the ChE family or the reactive tyrosine in hSA. In one embodiment, peptide has no fewer than 7 amino acids and no more than 41 amino acids. In one embodiment, peptide synthesis may be achieved by solid phase techniques. In another embodiment, peptide synthesis may be achieved by solution phase techniques.

The resulting peptides may be attached to the CP using standard techniques. These methods include, but are not limited to, the formation of amide bonds between the peptide and amine or carboxylic acid side chains of the CP or through the addition of a thiol to a modified CP to contain reactive maleimide groups. In one embodiment, the final product is a compound of Formula I.

Additional synthetic procedures are described in the Examples section, below.

Methods of Use

In one embodiment, the compounds of Formula I are used as immunogens for the generation of antibodies. The compounds are injected into rabbits, mice, or goats according to standard protocols to elicit antibody production. Isolated polyclonal antibodies recognize the original hapten and the entire protein that the hapten represents. In one embodiment, monoclonal antibodies are isolated using hybridoma techniques.

The thiocholine nerve agent analogs 18-23-Sp and 18-23-Rp react with human butyrylcholinesterase to yield adducts indistinguishable from those produced by authentic nerve agents. The MALDI-TOF spectra of tryptic digests of nerve agent-labeled human butyrylcholinesterase show the presence of unmodified peptides, adducted peptides, and aged peptides. None of the thiocholine compounds yielded evidence of new or unanticipated adducts. The mass balance between the unlabeled, adducted and aged peptides suggests that the lack of novel adducts from the thiocholine compounds is not the result of rapid aging of such adducts. Accordingly, the thiocholine-containing nerve agent analogs appear to give the same adducts as authentic nerve agents. Therefore, they are suitable substitutes for nerve agents in work that aims to study biological effects of nerve-agent modified proteins and diagnostic applications.

In one embodiment, provided are methods for using the compounds of Formula (I) to generate monoclonal or polyclonal antibodies specific for an OP-peptide.

In one embodiment, provided are methods for using antibodies against the compounds of Formula (I) to diagnose presence, identity and quantity of OP adducts in biological fluids in order to determine exposure to nerve agents, pesticides, or other active OP agents known to covalently modify proteins.

The isolated antibodies are used to identify an OP-adducted ChE or other esterase or hSA or other binding protein from human or animal samples. A variety of methods may be used for detection.

Biosensors have been developed using optical waveguides. The approach taken focuses on an optical biosensor system designed especially for simultaneous detection of multiple targets in multiple samples. Most optical biosensors have been developed as laboratory systems. Commercially available systems that have been partially automated include the BIACORE SPR™ system the ORIGEN™ electrochemiluminescence system, the IASYS™ resonant mirror system and the IMPACT™ displacement flow immunosensor. Each of these is unique in its fluidics system design. The Biacore flows the sample over the sensor surface in a single pass through a flow channel; measurements are made continuously, usually until there is no further signal change. The ORIGEN processes discrete samples individually by capturing the target from the solution on magnetic beads, collecting them on a magnet, adding the chemiluminescent substrate, and measuring the light output. The IAsys stirs the sample in a flow-through cuvette located over the resonant mirror and measures the signal as binding occurs. The IMPACT automatically collects saliva and passes it through minicolumns containing antibodies specific for drugs of abuse. In the presence of the drug, a fluorescent analog of the drug is displaced from the immobilized antibody and measured downstream. These systems can only discriminate multiple targets by sending the sample over parallel sensing surfaces; the Biacore SPR system has four parallel channels in the standard unit, the ORIGEN system can have eight, the IAsys comes with two cuvettes and the IMPACT accommodates ten flow columns.

In addition to the above described instruments for laboratory use, two optical biosensor systems, the FAST 6000™ and the RAPTOR™, have been commercialized for field operation. The FAST 6000 is a small (3.7 kg) displacement flow immunosensor for explosives and operates on the same principles as the IMPACT (Kusterbeck, 2002; Shriver-Lake et al., 2003). It is approximately the size of a laptop computer and automatically analyzes a manually added sample for up to six different targets with total assay times under two minutes. The RAPTOR fiber optic biosensor is portable (4.6 kg) and can automatically process samples added manually or pumped from a computer-controlled air sampler. The RAPTOR uses four optical fiber probes coated with antibodies to extract target from samples and generates a signal when a fluorescent tracer antibody binds to target captured by the antibody-coated probes. The entire operation, including data analysis and display, is automated (Jung et al., 2003). Because it uses a sandwich fluoroimmunoassay, it has proven to be highly resistant to interference from complex sample components (Anderson and Taitt, 2001; DeMarco et al., 1999; Golden et al., 1997), and the current version of the automated device is proving to be highly reliable (Jung et al., 2003). The main limitation of the RAPTOR is that it analyzes one sample at a time and is generally limited to the detection of only four targets, although the detection of eight targets has been recently reported (Anderson et al., 2004).

In comparison to the sensors described above, an array format offers a number of advantages, such as the potential to analyze a sample for a large number of targets simultaneously. Furthermore, inclusion of positive and negative controls on each sensing surface is more reliable than such controls located on parallel but separate sensing surfaces. DNA array technology has led this effort in terms of laboratory devices and two notable systems employing optical waveguides include the systems marketed by Zeptosens (Pawlak et al., 2002) and Illumina (Epstein and Walt, 2003). These systems accommodate thousands of capture molecules and are highly sensitive. However, they are designed for use by highly trained laboratory personnel and have not been automated or adapted for on-site applications.

Biosensors are widely touted as solutions to detection problems that can be used outside of the laboratory. Yet few biosensors have actually been made portable and sufficiently automated to accomplish that goal. Nonetheless, while portable systems have been slow to reach the field, the capabilities of laboratory biosensors continue to expand. As a consequence, the expectations of potential users continually increase. The Array Biosensor described herein combines optical waveguide technology and the capacity to test multiple samples simultaneously for multiple targets with portability and automation.

Naval Research Lab (NRL) has developed a biosensor based on a planar waveguide with sufficient surface area to accommodate many small ($mm^2$) sensing regions. The waveguide, a modified microscope slide, is illuminated using a 635 nm diode laser and a line generator, with the light launched into the proximal end. The first two-thirds of the slide provides a mode-mixing region so that the light is relatively uniform in the 2.4 $cm^2$ sensing region near the distal end (Feldstein et al., 1999). Under normal conditions, total internal reflection is achieved and an evanescent field is produced in the sensing region. The evanescent light excites fluorophores bound in the sensing region, and the emitted fluorescence is measured at 90° using a Peltier-cooled CCD camera (Wadkins et al., 1997; Golden et al., 2003). The location of the fluorescence within the array on the waveguide surface reveals the identity of the target detected.

In order to capture the target from the samples, antibodies or other molecules capable of binding to the target are immobilized on the waveguide surface in arrays of spots (Rowe et al., 1999; Delehanty et al., 2002). Both positive and negative controls can be included in the arrays to prevent false-positive or false-negative responses (Ligler et al., 2003). Furthermore, the use of multiple channels in combination with the arrays of sensor spots enables the analysis of multiple samples simultaneously. Assays can be formatted to detect either large molecules and microorganisms (sandwich assays) or small molecules (competitive assays, displacement assays) (Sapsford et al., 2002). The use of near-infrared fluorescence prevents interference from sample components, which may autofluoresce at shorter wavelengths, making separation of the target from complex samples unnecessary prior to analysis (Sapsford et al., 2001; Taitt et al., 2004). In contrast to mass-sensitive sensors, such as the surface plasmon resonance (SPR), resonant mirror, or interferometric systems (Homola et al., 2002; Kinning and Edwards, 2002; Campbell and McCloskey, 2002, Barzen et al., 2002), the fluorescence-based Array Biosensor requires a fluorophore-labeled molecule for signal generation. This makes the assay relatively immune to interference from nonspecific adsorption by sample components (Ligler et al., 2003; Rowe et al., 1999; Sapsford et al., 2001; Taitt et al., 2004).

Separation of the tracer and sample reservoir modules (1) facilitates lyophilization of the tracer reagents in the module, (2) eliminates the potential for sample and tracer mixing prior to the assay (which is important for preventing high dose hook effects), and (3) simplifies substitution of the sample module with connections to a continuous monitoring device.

Potential applications for on-site use of an Array Biosensor include detection of biohazardous and chemical hazardous agents, and this is the crux of this proposal. The capacity of the Array Biosensor to detect biomarkers in complex samples with little or no sample preparation has already been demonstrated using a non-automated prototype. Studies described herein will apply the automated system to determine how effectively the system can detect nerve agent-related biomarkers both in the laboratory and the field setting.

In summary, using a chemical biology approach, methods have been identified to selectively detect for OP exposure. This technology provides a valuable tool to diagnose and verify the actual type of OP exposure. This technology has the potential to help victims of OP exposure get the proper treatment in a timely manner.

The invention will be further described by the following examples, meant to illustrate but not limit the invention.

EXAMPLES

Example 1. General Procedure for Phosphonylation

A chilled solution of monochloride 6a-d shown below (4 mmol) and DMAP (0.4 mmol) in $CH_2Cl_2$ (8 mL) followed by diisopropylethylamine (4 mmol) in $CH_2Cl_2$ (5 mL) was added to a solution of Fmoc-Ser-OBn or Fmoc-Tyr-OBn (1 mmol) in $CH_2Cl_2$ (12 mL) stirring at 0° C. under argon. The reaction mixture was stirred at room temperature under argon. Reaction progress was monitored by TLC. When the reaction appeared to be complete, isopropanol was added to the mixture before the solvent was removed in vacuo. The crude product was purified by flash column chromatography (EtOAc/hexanes) to yield 9a-d or 11a-d as a mixture of diastereomers. Spectral data reflects the diastereomeric mixture.

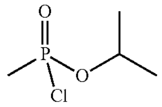

6a

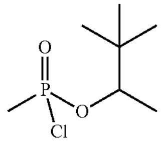

6b

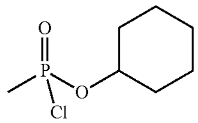

6c

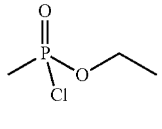

6d

Example 2. Fmoc-serine (O-isopropyl methylphosphonate) Benzyl Ester (9a)

50% yield as an oil; $^1$H NMR (500 Mz, $CDCl_3$) δ 1.26, 1.30 (d, J=6.2 Hz, 6H), 1.38, 1.41 (d, J=10.1 Hz, 3H), 4.24 (m, 1H), 4.33 (m, 2H), 4.42 (m, 2H), 4.62 (m, 1H), 4.68 (m, 1H), 5.24 (s, 2H), 6.04-6.22 (m, 1H), 7.36 (m, 9H), 7.40 (m, 2H), 7.76 (m, 2H); MS (ESI): m/z 538 (M+1), 560 (M+23).

Example 3. Fmoc-serine(O-pinacolyl methylphosphonate) Benzyl Ester (9b)

86% yield as a thick, yellow oil; $^1$H NMR (300 MHz, $CDCl_3$) δ 0.89 (s, 9H), 1.27 (d, J=6 Hz, 3H), 1.35 (m, 3H as diastereomeric mixture), 4.22, (m, 2H), 4.32 (m, 1H), 4.40 (m, 2H), 4.61 (m, 2H), 5.22 (s, 2H), 6.04-6.23 (m, 1H as diastereomeric mixture), 7.32 (m, 9H), 7.60 (m, 2H), 7.75 (m, 2H); $^{31}$P NMR (121.44 MHz, $CDCl_3$) δ 32.09, 32.77; MS (ESI): m/z 602 (M+23).

Example 4. Fmoc-serine(O-cyclohexyl methylphosphonate) Benzyl Ester (9c)

83% yield as a thick, pale, yellow residue; $^1$H NMR (300 MHz, $CDCl_3$) δ 1.31 (m, 4H), 1.39 (d, J=18 Hz, 3H), 1.49 (m, 2H), 1.66 (m, 2H), 1.88 (m, 2H), 4.22-4.47 (m, 5H), 4.59 (m, 2H), 5.22 (s, 2H), 6.03-6.21 (m, 1H, diastereomeric mixture), 7.34 (m, 9H), 7.60 (m, 2H), 7.75 (m, 2H); $^{31}$P NMR (121.44 MHz, $CDCl_3$) δ 32.13; MS (ESI): m/z 600 (M+23).

Example 5. Fmoc-serine(O-ethyl methylphosphonate) Benzyl Ester (9d)

Clear oil; 75% yield; $^1$H NMR (300 MHz, $CDCl_3$) □ 1.28 (t, J=7 Hz, 3H), 1.41 (d, J=18 Hz, 3H), 4.05 (m, 2H), 4.25 (m, 1H), 4.36 (m, 1H), 4.42 (m, 2H), 4.48 (m, 1H), 4.64 (m, 1H), 5.24 (s, 2H), 6.11 (m, 1H), 7.37 (m, 9H), 7.62 (m, 2H), 7.78 (d, J=7 Hz, 2H); $^{31}$P NMR (202 MHz, $CDCl_3$) □ 32.48; MS (ESI): m/z 546 ($M^+$+23).

Example 6. Fmoc-tyrosine(O-isopropyl methylphosphonate) Benzyl Ester (11a)

White foam; 66% yield; $^1$H NMR (300 MHz, $CDCl_3$) δ 1.24 (d, J=6 Hz, 3H), 1.34 (d, J=6 Hz, 3H), 1.57 (d, J=18 Hz, 3H), 3.07 (m, 2H), 4.19 (m, 1H), 4.37 (m, 2H), 4.68 (m, 1H), 4.79 (sxt, J=6 Hz, 1H), 5.15 (m, 2H), 5.27 (m, 1H), 6.93 (d, J=6 Hz, 2H), 7.03 (d, J=6 Hz, 2H), 7.35 (m, 9H), 7.56 (d, J=6 Hz, 2H), 7.76 (d, J=6 Hz, 2H); $^{31}$P NMR (121.4 MHz, $CDCl_3$) δ 27.65; MS (ESI): m/z 636 ($M^+$+23).

Example 7. Fmoc-tyrosine(O-pinacolyl methylphosphonate) Benzyl Ester (11b)

Clear oil; 73% yield; $^1$H NMR (300 MHz, $CDCl_3$) δ 0.89 (s, 9H), 1.29 (d, J=6 Hz, 3H), 1.48 (d, J=15 Hz, 3H), 3.05 (m, 2H), 4.18 (m, 2H), 4.32 (m, 1H), 4.67 (m, 2H), 5.14 (m, 2H), 5.70 (m, 1H), 6.92 (d, J=6 Hz, 2H), 7.03 (d, J=6 Hz, 2H), 7.30 (m, 9H), 7.52 (d, J=6 Hz, 2H), 7.73 (d, J=6 Hz, 2H); $^{31}$P NMR (121.4 MHz, $CDCl_3$) δ 27.47, 28.55, 30.34, 33.40; MS (ESI): m/z 678 ($M^+$+23).

Example 8. Fmoc-tyrosine(O-cyclohexyl methylphosphonate) Benzyl Ester (11c)

Clear oil; 85% yield; $^1$H NMR (300 MHz, $CDCl_3$) δ 1.36 (m, 4H), 1.52 (d, J=18 Hz, 3H), 1.61 (m, 2H), 1.83 (m, 2H), 1.94 (m, 2H), 3.08 (m, 2H), 4.39 (m, 1H), 4.43 (m, 2H), 4.52 (m, 1H), 4.69 (m, 1H), 5.17 (m, 2H), 5.28 (d, J=6 Hz, 1H), 6.92 (d, J=6 Hz, 2H), 7.05 (d, J=6 Hz, 2H), 7.36 (m, 9H), 7.55 (d, J=6 Hz, 2H), 7.76 (d, J=6 Hz, 2H); $^{31}$P NMR (121.4 MHz, $CDCl_3$) δ 27.72, 29.64; MS (ESI): m/z 676 ($M^+$+23).

Example 9. Fmoc-tyrosine(O-ethyl methylphosphonate) Benzyl Ester (11d)

Yellow foam; 77% yield; $^1$H NMR (300 MHz, $CDCl_3$) δ 1.3 (t, J=6 Hz, 3H), 1.56 (d, J=18 Hz, 3H), 3.08 (t, J=6 Hz, 2H), 4.2 (m, 2H), 4.38 (m, 2H), 4.68 (m, 1H), 5.14 (m, 2H), 5.36 (d, J=6 Hz, 1H), 6.93 (d, J=9 Hz, 2H), 7.04 (d, J=9 Hz, 2H), 7.35 (m, 9H), 7.56 (d, J=6 Hz, 2H), 7.75 (d, J=6 Hz, 2H); $^{31}$P NMR (121.4 MHz, $CDCl_3$) δ 28.82; MS (ESI): m/z 624 ($M^+$+24).

Example 10. General Procedure for Hydrogenation of Benzyl Esters

Benzyl esters 9a-d and 11a-d (0.25 mmol) were dissolved in a 1:1 mixture of THF/MeOH (8 mL). Pd/C (40 mg, 10% dry basis, wet, Degussa type E101 NEW) was added. The suspension was evacuated and purged with argon before hydrogen gas was bubbled through the mixture at a moderate rate. After 45 min, the system was purged with argon; the suspension was filtered through a bed of Celite; and the Celite cake was washed extensively with THF until the free acid was washed out of the filter when checked by TLC. The filtrate was concentrated in vacuo. The crude product was purified by column chromatography (100% EtOAc then with $CHCl_3$/MeOH/AcOH 90:8:2) to yield the free acid 10a-d or 12a-d as a diastereomeric mixture.

Example 11. Fmoc-serine(O-isopropyl methylphosphonate) (10a)

77% yield as a foam; $^1$H NMR (300 MHz, $CDCl_3$) δ 1.31 (d, J=6 Hz, 6H), 1.51 (d, J=18 Hz, 3H), 4.21 (m, 1H), 4.36 (m, 2H), 4.57 (m, 2H), 4.72 (m, 2H), 6.05-6.21 (m, 1H, diastereomeric mixture), 7.29 (m, 2H), 7.38 (m, 2H), 7.59 (m, 2H), 7.75 (m, 2H); $^{31}$P NMR (121.44 MHz, $CDCl_3$) δ 32.32, 33.08; MS (ESI): m/z 470 (M+23).

Example 12. Fmoc-serine(O-pinacolyl methylphosphonate) (10b)

47% yield as a foam; $^1$H NMR (300 MHz, $CDCl_3$) δ 0.91 (s, 9H), 1.27 (m, 3H), 1.54 (d, J=18 Hz, 3H), 4.22-4.40 (m, 5H), 4.59 (m, 2H), 6.05-6.22 (m, 1H, diastereomeric mixture), 7.31 (m, 2H), 7.40 (m, 2H), 7.62 (m, 2H), 7.76 (m, 2H); $^{31}$P NMR (121.44 MHz, $CDCl_3$) δ 33.01, 33.67; MS (ESI): m/z 512 (M+23).

Example 13. Fmoc-serine(O-cyclohexyl methylphosphonate) (10c)

72% yield as a clear residue; $^1$H NMR (300 MHz, $CDCl_3$) δ 1.30 (m, 4H), 1.49 (m, 2H), 1.54 (d, J=18 Hz, 3H), 1.69 (m, 2H), 1.87 (m, 2H), 4.22 (m, 2H), 4.35 (m, 3H), 4.57 (m, 2H), 6.02-6.22 (m, 1H, diastereomeric mixture), 7.29 (m, 2H), 7.38 (m, 2H), 7.60 (m, 2H), 7.75 (m, 2H); $^{31}$P NMR (121.44 MHz, $CDCl_3$) δ 32.21, 33.09; MS (ESI): m/z 487 (Mt), 510 (M+23).

Example 14. Fmoc-serine(O-ethyl methylphosphonate) (10d)

Colorless residue; 87% yield; $^1$H (300 MHz, $CDCl_3$) δ 1.30 (t, J=7 Hz, 3H), 1.52 (d, J=18 Hz, 3H), 4.09 (m, 2H), 4.20 (m, 1H), 4.31 (m, 1H), 4.37 (m, 2H), 4.58 (m, 2H), 6.15 (d, J=7 Hz, 0.6H), 6.26 (d, J=7 Hz, 0.4H), 7.29 (m, 2H), 7.38 (m, 2H), 7.6 (m, 2H), 7.76 (m, 2H); $^{31}$P NMR (202 MHz, $CDCl_3$) δ 32.69, 33.45; MS (ESI): m/z 456 ($M^+$+23).

Example 15. Fmoc-tyrosine(O-isopropyl methylphosphonate) (12a)

Clear oil; 85% yield; $^1$H NMR (300 MHz, $CDCl_3$) δ 1.22 (d, J=6 Hz, 3H), 1.32 (d, J=6 Hz, 3H), 1.62 (dd, J=6, 18 Hz, 3H), 3.14 (m, 2H), 4.19 (m, 2H), 4.33 (m, 1H), 4.45 (m, 1H), 4.67 (m, 1H), 4.8 (m, 1H), 7.10 (m, 4H), 7.3 (m, 2H), 7.39 (m, 2H), 7.57 (m, 2H), 7.74 (d, J=9 Hz, 2H); $^{31}$P NMR (121.4 MHz, $CDCl_3$) δ 28.65; MS (ESI): m/z 546 ($M^+$+23)

Example 16. Fmoc-tyrosine(O-pinacolyl methylphosphonate) (12b)

Tan oil; 62% yield; $^1$H NMR (300 MHz, $CDCl_3$) δ 0.90 (s, 9H), 1.29 (d, J=6 Hz, 3H), 1.45 (d, J=18 Hz, 3H), 3.14 (m, 2H), 4.2 (m, 2H), 4.32 (m, 1H), 4.44 (m, 1H), 4.66 (m, 2H), 5.39 (m, 1H), 7.09 (br s, 4H), 7.34 (m, 4H), 7.56 (d, J=6 Hz, 2H), 7.75 (d, J=6 Hz, 2H); $^{31}$P NMR (121.4 MHz, $CDCl_3$) δ 30.46; MS (ESI): m/z 588 ($M^+$+23).

Example 17. Fmoc-tyrosine(O-cyclohexyl methylphosphonate) (12c)

Tan oil; 0.34 g (60%); $^1$H NMR (500 MHz, $CDCl_3$) δ 1.3 (m, 4H), 1.43-1.53 (m, 2H), 1.63 (d, J=18 Hz, 3H), 1.7 (m, 2H), 1.92 (m, 2H), 3.16 (m, 2H), 4.22 (m, 1H), 4.34 (m, 1H), 4.47 (m, 2H), 4.66 (m, 1H), 5.5 (m, 1H), 7.1 (m, 4H), 7.31 (m, 2H), 7.39 (m, 2H), 7.58 (m, 2H), 7.76 (m, 2H); $^{31}$P NMR (202 MHz, $CDCl_3$) δ 27.52, 28.12; MS (ESI): m/z 586 ($M^+$+23).

Example 18. Fmoc-tyrosine(O-ethyl methylphosphonate) (12d)

White foam; 41% yield; $^1$H NMR (300 MHz, $CDCl_3$) δ 1.29 (t, J=6 Hz, 3H), 1.64 (dd, J=6, 18 Hz, 3H), 3.16 (m, 2H), 4.2 (m, 3H), 4.34 (m, 1H), 4.47 (m, 1H), 4.69 (m, 1H), 5.56 (m, 1H), 7.1 (m, 4H), 7.28 (m, 2H), 7.4 (m, 2H), 7.57 (m, 2H), 7.75 (d, J=6 Hz, 2H); $^{31}$P NMR (121.4 MHz, $CDCl_3$) δ 29.81; MS (ESI): m/z 532 ($M^+$+23).

Example 19. Solid Phase Synthesis of Phosphonylated Peptides

Solid-phase peptide synthesis was done using an Advanced ChemTech ACT-3926 peptide synthesizer. The peptides were synthesized using Fmoc chemistry on a 2-chlorotrityl resin. Protected amino acids used in the peptide synthesis included Fmoc-glutamic acid with the isopropyl phenyl ester on the carboxylic acid side chain and Fmoc-lysine with additional Fmoc protection of the amine side chain. Fmoc-protected amino acids were activated with HBTU/HOBt. Peptide synthesis was done on an automated synthesizer up to the residue preceding the phosphonylated amino acid. After this point in the synthesis, couplings were done manually to ensure the highest coupling efficiency. Cleavage from the resin was achieved by treating the peptide-resin with 1% TFA/$CH_2C_{12}$ containing 2% triisopropylsilane overnight at room temperature. Crude phosphonylated peptide reaction products were purified by reversed-phase HPLC on a C18 column (0.1% TFA water/acetonitrile). Peptide purity was >90% and was verified by analytical HPLC and mass spectrometry. Examples of peptide sequences are shown in Table 1 and Table 2 (below).

TABLE 1

Phosphonylated peptides corresponding to the active site peptide of phosphonylated BuChE.

| OP-Peptide Name | OP-Peptide Sequence[a] | MW obs.[b] | MW calc.[b] |
|---|---|---|---|
| BuChE-sarin SEQ ID No: 1 | $H_2N$-Lys-Ser-Val-Thr-Leu-Phe-Gly-Glu-Ser[P═O($CH_3$)(O-iPr)]-Ala-Gly-Ala-Ala-OH | 1470.8 | 1470.6 |
| BuChE-soman SEQ ID No: 2 | $H_2N$-Lys-Ser-Val-Thr-Leu-Phe-Gly-Glu-Ser[P═O($CH_3$)(O-Pinacolyl)]-Ala-Gly-Ala-Ala-OH | 1513.4 | 1512.7 |
| BuChE-GF SEQ ID No: 3 | $H_2N$-Lys-Ser-Val-Thr-Leu-Phe-Gly-Glu-Ser[P═O($CH_3$)(O-cyclohexyl)]-Ala-Gly-Ala-Ala-OH | 1511.3 | 1510.7 |
| BuChE-VX SEQ ID No: 4 | $H_2N$-Lys-Ser-Val-Thr-Leu-Phe-Gly-Glu-Ser[P═O($CH_3$)(O-ethyl])-Ala-Gly-Ala-Ala-OH | 1457.2 | 1456.6 |

[a]The seine residue modified at its hydroxyl side chain group by the indicated organophosphate compound corresponds to Ser-198 in the human butylcholine esterase protein.
[b]Molecular weight (MW) is for the indicated OP-peptide having amino caproic acid linker attached by its amino terminus to the OP-peptide C-terminus through an amide bond.

TABLE 2

Phosphonylated peptides corresponding to the phosphonylated peptide of human serum albumin (HSA).

| OP-Peptide Name | OP-Peptide Sequence[a] | MW obs.[b] | MW calc.[b] |
|---|---|---|---|
| HSA-sarin SEQ ID No: 5 | Tyr[P═O($CH_3$)(O-iPr)]-Thr-Lys-Lys-Val-Pro-Gln-OH | 1465.4 | 1465.7 |
| HSA-soman SEQ ID No: 6 | $H_2N$-Leu-Val-Arg-Tyr[P═O($CH_3$)(O-Pinacolyl)]-Thr-Lys-Lys-Val-Pro-Gln-OH | 1507.4 | 1507.8 |
| HSA-GF SEQ ID No: 7 | $H_2N$-Leu-Val-Arg-Tyr[P═O($CH_3$)(O-cyclohexyl)]-Thr-Lys-Lys-Val-Pro-Gln-OH | 1505.3 | 1505.8 |
| HSA-VX SEQ ID No: 8 | $H_2N$-Leu-Val-Arg-Tyr[P═O($CH_3$)(O-ethyl)]-Thr-Lys-Lys-Val-Pro-Gln-OH | 1451.3 | 1451.7 |

[a]The tyrosine residue modified at its penolic side chain group by the indicated organophosphate compound corresponds to Tyr-411 in the human serum albumin protein.
[b]Molecular weight (MW) is for the indicated OP-peptide having amino caproic acid linker attached by its amino terminus to the OP-peptide C-terminus through an amide bond.

Example 20. Synthesis of (2Sp,4R,5S) and (2Rp, 4R,5S)-trimethyl-5-phenyl-1,3,2-oxazaphospholidine-2-thione (14-Sp and 14-Rp) (Scheme 3)

A solution of methylphosphonothioic dichloride 7a (10.0 g, 49.6 mmol) in toluene (40 mL) was added slowly to a solution of (+)-ephedrine hydrochloride 13 (7.39 g, 49.6 mmol) dissolved in toluene (260 mL) and triethylamine (50 mL). The mixture was stirred at room temperature overnight. The mixture was then filtered, washed with water (2 times), dried over sodium sulfate, and concentrated in vacuo. The crude product was purified by silica gel column chromatography (hexanes/ethyl acetate, 9:1, v:v) to yield 2.0 g (white solid, 17%) of 14-$S_p$ followed by 1.5 g (white solid, 13%) of 14-$R_p$. The purity of the enantiomers (14-$S_p$ and 14-$R_p$) was determined to be >95% by $^1$H-NMR analysis: (14-$S_p$), $^1$H-NMR (300 MHz, $CDCl_3$) δ: 7.27-7.39 (m, 5H), 5.67 (dd, J=5.9, 2.3 Hz, 3H), 3.63 (apparent septet, 1H), 2.77 (d, J=12.1 Hz, 3H), 2.07 (d, J=14.6 Hz, 3H), 0.75 (d, J=6.6 Hz, 3H); and (14-$S_p$), $^1$H-NMR (300 MHz, $CDCl_3$) δ: 7.29-7.40 (m, 5H), 5.48 (dd, J=5.6, 3.4 Hz, 3H), 3.63 (m, 1H), 2.68 (d, J=12.7 Hz, 3H), 1.95 (d, J=14.0 Hz, 3H), 0.82 (d, J=6.3 Hz, 3H).

Example 21. General Preparation of Rp- and Sp-alkylthiophosphonic Acids (15-Sp,16-Sp,17-Sp,15-Rp,16-Rp.17-Rp)

A 1:1 mixture by volume of the requisite alcohol (ROH=a: isopropanol, b: cyclohexanol, c: 3,3-dimethyl-2-butanol) saturated with anhydrous hydrochloric acid and 2-butanone (3 mL) was added to individual solutions of 14 ($S_p$ or $R_p$, 500 mg, 2.07 mmol) in 2-butanone (3.5 mL) at 0° C. The reaction mixture was allowed to warm to room temperature and was stirred for 1 hour. The mixture was then poured into 10% aq. sodium carbonate (12.5 mL), diluted with water (25 mL) and ethanol (40 mL). Pd/C (50 mg) was added and the reaction mixture was stirred under an atmosphere of $H_2$ gas overnight at room temperature. The mixture was then flushed with $N_2$ gas, filtered, and concentrated to remove the ethanol. The remaining aqueous mixture was diluted with water (10 mL) and extracted with diethyl ether (30 mL, 3 times). The organic layer was discarded. The aqueous layer was then acidified to pH<3 with citric acid and extracted with 4:1 chloroform/isopropyl alcohol (15 mL, 5 times). The organic layer was dried over sodium sulfate, filtered, and concentrated in vacuo to afford the product as a clear viscous oil with the following yield: (15-$S_p$), 200 mg (63%); (15-$R_p$), 225 mg, (71%); (16-$S_p$), 270 mg (67%); (16-$R_p$), 313 mg (78%); (17-$S_p$), 152 mg (37%); and (17-$R_p$), 352 mg (86%). The crude product was used without further purification after NMR verification: (15), $^1$H-NMR (300 MHz, $CDCl_3$) δ: 7.70 (br s, 1H), 4.78 (septet, J=6.0 Hz, 1H), 1.70 (d, J=15.0 Hz, 3H), 1.25 (apparent triplet, J=6.0 Hz, 6H); (16), $^1$H-NMR (300 MHz, $CDCl_3$) δ: 8.11 (br s, 1H), 4.50 (m, 1H), 1.88 (m, 2H), 1.73 (d, J=15.0 Hz, 3H), 1.19-1.63 (m, 8H); and (17), $^1$H-NMR (300 MHz, $CDCl_3$) (2:1 mixture of diastereomers, major diastereomer) δ: 5.13 (br s, 1H), 4.33-4.43 (m, 1H), 1.70 (d, J=15.0 Hz, 3H), 1.22 (apparent triplet, J=6.0 Hz, 3H), 0.89 (s. 9H); (minor diastereomer, diagnostic peaks) δ: 1.77 (d, J=15.0 Hz, 3H), 1.09 (apparent triplet, J=6.0 Hz, 3H), 0.90 (s. 9H).

Example 22. General Preparation of Rp and Sp O-alkyl S-dimethylaminoethyl Methylphosphonothioates (18-$S_p$,18-$R_p$,19-$S_p$,19-$R_p$,20-$S_p$,20-$R_p$)

To the corresponding thiophosphonic acid (15-$S_p$: 300 mg, 1.95 mmol, 15-$R_p$: 313 mg, 2.03 mmol, 16-$S_p$: 346 mg, 1.78 mmol, 16-$R_p$: 419 mg, 2.16 mmol, 17-$S_p$: 382 mg, 1.95 mmol, 17-$R_p$: 447 mg, 2.28 mmol) in ethanol (5 mL) and 10% aq. sodium carbonate (8 mL) was added (2-iodoethyl) dimethylamine hydroiodide (1.0 equiv). The reaction mixture was stirred at room temperature overnight. The mixture was then poured into brine and extracted into dichloromethane. The organic layer was concentrated to yield a crude oil that was purified by silica gel flash column chromatography (0-30% methanol in dichloromethane v:v, Teledyne ISCO COMBIFLASH™ Rf system, Newark, Del.) to afford the products as clear oils. The purity was determined to be >95% by $^1$H-NMR analysis. The overall yield and compound verification are as follows: (18-$S_p$) 140 mg (32%), (18-$R_p$) 178 mg (39%), (19-$S_p$) 149 mg (32%), (19-$R_p$) 210 mg (43%), (20-$S_p$) 130 mg (25%), (20-$R_p$) 178 mg (34%); (18), $^1$H-NMR (500 MHz, $CDCl_3$) δ: 4.72-4.78 (m, 1H), 2.90-3.01 (m, 2H), 2.54-2.62 (m, 2H), 2.26 (s, 6H), 1.75 (d, J=15.8 Hz, 3H), 1.30 (dd, J=6.3, 30.6 Hz, 6H); $^{31}$P-NMR (200 MHz, $CDCl_3$) δ: 53.1; (18-$S_p$), $[\alpha]^{25}_D$−21.3° (c 0.020, $CH_3CN$); (18-$R_p$), $[\alpha]^{25}_D$+49.7° (c 0.009, $CH_3CN$); $R_f$ (9:1 $CH_2Cl_2$:$CH_3OH$)=0.35; (19), $^1$H-NMR (500 MHz, $CDCl_3$) δ: 4.50-4.43 (m, 1H), 2.89-3.03 (m, 2H), 2.57-2.66 (m, 2H), 2.28 (s, 6H), 1.93-1.99 (m, 1H), 1.86-1.91 (m, 1H), 1.77 (d, J=15.8 Hz, 3H), 1.67-1.74 (m, 2H), 1.42-1.56 (m, 3H), 1.27-1.36 (m, 2H), 1.15-1.24 (m, 1H); $^{31}$P-NMR (200 MHz, $CDCl_3$) δ: 53.0; (19-$S_p$), $[\alpha]^{25}_D$−26.0° (c 0.03, $CH_3C$); (19-$R_p$), $[\alpha]^{25}_D$+34.0° (c 0.021, $CH_3CN$; $R_f$ (9:1 $CH_2Cl_2$:$CH_3OH$)=0.34; (20), $^1$H-NMR (500 MHz, $CDCl_3$) (major diastereomer) δ: 4.25-4.32 (m, 1H), 2.95-3.12 (m, 2H), 2.64-2.74 (m, 2H), 2.34 (s, 6H), 1.79 (d, J=15.8 Hz, 3H), 1.34, (d, J=6.3 Hz, 3H), 0.89 (s, 9H); (minor diastereomer's diagnostic peaks) δ: 4.30-4.35 (m, 1H), 1.28, (d, J=6.6 Hz, 3H), 0.91 (s, 9H); $^{31}$P-NMR (200 MHz, $CDCl_3$) δ: 53.3; (20-$S_p$), $[\alpha]^{25}_D$−14.4° (c 0.008, $CH_3CN$); (20-$R_p$), $[\alpha]^{25}_D$+28.4° (c 0.01, $CH_3CN$); $R_f$ (9:1 $CH_2Cl_2$:$CH_3OH$)=0.32.

Example 23. General Synthesis of Rp and Sp 2-(O-alkyl(methyl)phosphorylthio)-N,N,N-trimethylethanaminium Iodide (21-Sp,21-Rp,22-Sp,22-Rp,23-Sp, 23-Rp)

To a solution of 18-20 (18-$S_p$: 70 mg, 0.31 mmol, 18-$R_p$: 60 mg, 0.27 mmol, 19-$S_p$: 35 mg, 0.13 mmol, 19-$R_p$: 30 mg, 0.11 mmol, 20-$S_p$: 6 mg, 0.02 mmol, 20-$R_p$: 6 mg, 0.02 mmol) in benzene (1 mL) was added iodomethane (1 mL). This solution was allowed to stand at room temperature overnight and then concentrated and dried under high-vacuum to afford pure product as clear-light yellow oils. The purity was determined to be >95% by $^1$H-NMR analysis. The overall yield and compound verification are as follows: (21-$S_p$) 109 mg (96%), (21-$R_p$) 69 mg (70%), (22-$S_p$) 50 mg (94%), (22-$R_p$) 10 mg (22%), (23-$S_p$) 6.5 mg (71%), (23-$R_p$) 5.8 mg (63%); (21), $^1$H-NMR (500 MHz, $CD_3OD$) δ: 4.79-4.82 (m, 1H), 3.62-3.69 (m, 2H), 3.25-3.32 (m, 2H), 3.19 (s, 9H), 1.91 (d, J=20.0 Hz, 3H), 1.37 (dd, J=20.0, 5.0 Hz, 3H); $^{31}$P-NMR (200 MHz, $CD_3OD$) δ: 54.6; (22), $^1$H-NMR (500 MHz, $CD_3OD$) δ: 4.49-455 (m, 1H), 3.61-3.69 (m, 2H), 3.21-3.32 (m, 2H), 3.18 (s, 9H), 1.9-1.96 (2H), 1.92 (d, J=15.0 Hz, 3H), 1.74-1.76 (m, 2H), 1.53-1.58 (m, 3H), 1.26-1.41 (m, 3H); $^{31}$P-NMR (200 MHz, $CD_3OD$) δ: 54.7; (23), $^1$H-NMR (500 MHz, $CD_3OD$) major diastereomer δ: 4.31-4.37 (m, 1H), 3.59-3.68 (m, 2H), 3.22-3.32 (m, 2H), 3.18 (s, 9H), 1.93 (d, J=15.0 Hz, 3H), 1.32-1.39 (m, 3H), 0.92 (apparent t, J=10.0 Hz, 9H); $^{31}$P-NMR (200 MHz, $CD_3OD$) δ: 54.9.

Example 24. Synthesis of (2Rp,4R,5S) and (2Sp, 4R,5S)-chlorodimethyl-5-phenyl-1,3,2-oxazaphospholidine-2-thione (24-Rp and 24-Sp)

A solution of thiophosphoryl chloride 7b (4.2 mL, 41 mmol) in toluene (25 mL) was slowly added to a slurry of (+)-ephedrine 13 (8.60 g, 43 mmol) and triethylamine (35 mL) in toluene (150 mL). The mixture was stirred at room temperature overnight and then poured in ethyl acetate and extracted with water (3 times). The organic layer was dried over sodium sulfate, filtered, and concentrated in vacuo to afford a yellow oil that solidified upon standing. The crude material was found to be a 3:1 mixture of the Rp:Sp isomers. Purification of the crude mixture consisted of passing the material through a silica column (4 inch height by 3 inch diameter) using dichloromethane as eluent followed by silica gel flash column chromatography (0-10% ethyl acetate/hexanes, v:v) to give 1.60 g (15%) of 24-$R_p$ (top spot) and 5.52 g (53%) of 24-$S_p$ (bottom spot). The purity of the enantiomers (24-$S_p$ and 24-$R_p$) was determined to be >95% by $^1$H-NMR analysis: (24-$R_p$), $^1$H-NMR (300 MHz, $CDCl_3$) δ: 7.30-7.44 (m, 5H), 5.83 (d, J=6.6 Hz, 1H), 3.83 (dquint, 1H), 2.92 (d, J=14.6 Hz, 3H), 0.88 (d, J=6.9 Hz, 3H); and (24-$S_p$), $^1$H-NMR (300 MHz, $CDCl_3$) δ: 7.32-7.41 (m, 5H), 5.60 (t, 7.3 Hz, 1H), 3.75 (sextet, J=6.0 Hz, 1H), 2.73 (d, J=16.8 Hz, 3H), 0.80 (d, J=6.6 Hz, 3H).

Example 25. Synthesis of (2Sp,4R,5S) and (2Rp, 4R,5S)—N,N-dimethylamino-dimethyl-5-phenyl-1, 3, 2-oxazaphospholidine-2-thione (25-Sp and 25-Rp)

A solution of 24 ($S_p$ or $R_p$ isomer, 1.00 g, 3.82 mmol) in dry toluene (10 mL) in a pressure tube was bubbled with anhydrous dimethylamine gas. After 1 minute, the tube was sealed and stirred at room temperature. After 4 hours, the mixture was filtered, diluted with ethyl acetate, and washed with water (2 times). The organic layer was dried over sodium sulfate, filtered, and concentrated in vacuo to afford 25-$S_p$ (1.03 g, 100%) or 25-$R_p$ (1.03 g, 100%) as a yellow oil. The crude material was used without further purification. The purity of the enantiomers (25-$S_p$ and 25-$R_p$) was determined to be >95% by $^1$H-NMR analysis: $^1$H-NMR (300 MHz, $CDCl_3$) δ: 7.28-7.38 (m, 5H), 5.67 (d, J=6.9 Hz, 1H), 3.53 (sextet, J=6.0 Hz, 1H), 2.95 (s, 3H), 2.91 (s, 3H), 2.60 (d, J=11.8 Hz, 3H), 0.75 (d, J=6.6 Hz, 3H).

Example 26. Synthesis of Sp and Rp O-ethyl O-hydrogen dimethylphosphor-amidothioate (26-Sp and 26-Rp)

To a solution of 25-$S_p$ (500 mg, 1.85 mmol) or 25-$R_p$ (503 mg, 1.86 mmol) in absolute ethanol (2 mL) was added a solution of ethanol (2 mL) saturated with hydrogen chloride. After stirring at room temperature for 2 hours, the mixture was basified to pH-12 with aq. sodium hydroxide (10N) and stirred at room temperature overnight. The mixture was extracted with diethyl ether (3 times). The organic layer was discarded and the aqueous layer acidified to pH<3 with citric acid and extracted with 4:1 chloroform/isopropyl alcohol (3 times). The organic layer was dried over sodium sulfate, filtered, and concentrated in vacuo to afford 26-$S_p$ (308 mg, 98%) or 26-$R_p$ (315 mg, 100%) as a clear viscous oil. The crude material was used without further purification. The purity of the enantiomers (24-$S_p$ and 24-$R_p$) was determined to be >95% by $^1$H-NMR analysis: $^1$H-NMR (300 MHz, $CD_3OD$) δ: 3.60 (quart, J=7.5 Hz, 2H), 2.82 (s, 3H), 2.79 (s, 3H), 1.32 (t, J=7.5 Hz, 3H).

Example 27. Synthesis of Sp and Rp 2-((dimethylamino)(ethoxy)-phosphorylthio)-N,N,N-trimethylethanaminium Iodide (27-Sp and 27-Rp) (Scheme 2)

To a solution of 26-$S_p$ (645 mg, 3.81 mmol) or 26-$R_p$ (315 mg, 1.86 mmol) in ethanol (10 mL) and 10% aq. sodium carbonate (10 mL) was added (2-iodoethyl)dimethylamine hydroiodide (1.0 equiv.). The reaction mixture was stirred at room temperature overnight then poured into brine and extracted with dichloromethane (3 times). The organic layer containing (S)—S-2-(dimethylamino)ethyl O-ethyl dimethylphosphoramidothioate (27-$S_p$ or 27-$R_p$) was concentrated to ~3 mL then diluted with benzene (3 mL) and excess methyl iodide (3 mL) was added. The mixture was allowed to sit without stirring at room temperature overnight. The solid precipitate 28-$S_p$ (127 mg, 9%) or 28-$R_p$ (67 mg, 9%) was collected by decanting the liquid and drying under high vacuum. The purity of the enantiomers (27-$S_p$ and 27-$R_p$) was determined to be >95% by $^1$H-NMR analysis: $^1$H-NMR (500 MHz, $CD_3OD$) δ: 4.12-4.20 (m, 4H), 3.76 (t, J=9.0 Hz, 2H), 3.34 (s, 9H), 2.78 (s, 3H), 2.74 (s, 3H), 1.36 (t, J=9.0 Hz, 3H); $^{31}$P-NMR (200 MHz, $CDCl_3$) δ: 35.7.

Example 28. Conjugation of Peptides to Maleimide-Activated KLH

The peptide OP modified or native control peptide was dissolved in water at a concentration 10 mg/mL. This solution (10 μL, 1 mg) was added to maleimide-activated KLH lyophilized from PBS (4.3 mg total weight) dissolved in 69 μL water. The resulting clear solution was kept at room temperature. Reaction progress was monitored by TLC to check for disappearance of peptide. After 24 h, the sample was transferred to a Slide-a-lyzer dialysis cassette MWCO 3500 (Pierce Chemical Co.) and dialyzed against PBS at 4° C. Protein concentration was determined by the BCA assay. This conjugation was combined with earlier conjugations for antibody generation.

Example 29. General Method for the Production of Monoclonal Antibodies to OP Peptide Adducts Antigens comprised of native and OP-conjugated peptides coupled to KLH carrier protein were used to immunize mice (three mice per antigen), followed by screening of test bleeds against the immunizing antigen to identify sera with high IgG titer and low IgM titer. Once the titers were at acceptable levels, the spleen cells from those mice were fused with myeloma cells. The hybrid cells were then screened against the antigen to identify and isolate cell clones that produce antibody with the desired selectivity. Positive clones went through two rounds of subcloning followed by ELISA testing to ensure purity of cells expressing the appropriate antibodies. Shown in Table 3, generation of the first monoclonal antibody, specific for BChE-sarin with sensitivity to at least 1:1000 dilution, was achieved.

TABLE 3

Summary of OP-adducted BChE antigens and hybridoma formation

| HBRI compound | OP adduct | adduct ELISA #1 | Sub-clone #1 | adduct ELISA #2 | Sub-clone #2 | Final adduct ELISA |
|---|---|---|---|---|---|---|
| MTM-III-004 | Sarin | ✓ | ✓ | ✓ | ✓ | ✓ |
| MTM-III-018 | VX | ✓ | ✓ | ✓ | ✓ | ✓ |
| MTM-III-019 | soman | ✓ | ✓ | ✓ | ✓ | ✓ |
| MTM-III-040 | GF | ✓ | ✓ | ✓ | ✓ | ✓ |
| MTM-II-195 | none (control) | ✓ | ✓ | ✓ | ✓ | ✓ |

Example 30. Hybridoma Cell Growth

Hybridoma cell lines were aliquoted in multiple vials and stored in liquid nitrogen. Vials were quick-thawed (1-2 min.) at 37° C. and mixed with RPMI medium/10% fetal bovine serum (FBS). Cells were collected by low-speed centrifugation, resuspended in fresh medium, counted using trypan blue stain to determine concentration and viability, and plated to an optimal concentration of 0.2-0.3×$10^6$ cells per ml. Cultures were maintained in RPMI-1640 medium supplemented with 10% FBS (v/v), glutamine and Pen/Strep, and were gradually expanded to T175 (175 $cm^2$) flasks as required. To ensure the viability of the cells and their specific function, a regular schedule of subculturing and monitoring was followed. Since most hybridoma cell lines are semi-adherent, both floating and scraped adherent cells from flasks were harvested for routine passage. Upon culture expansion, replicate vials containing 4×$10^5$ cells/ml in FBS/20% DMSO were frozen and stored in liquid nitrogen.

Example 31. ELISA Assays

Culture media is tested to confirm production of appropriate mAb by indirect ELISA using appropriate native and OP-conjugated peptides, KLH carrier protein, and non-hybridoma media as controls. High-binding 96-well flat bottom ELISA plates are coated with 1 μg/well of antigen overnight at 4° C. Following several washes with PBS/Tween-20 (PBST), wells are blocked with 1% cold fish gelatin for one hour at room temp. After several PBST washes, serial dilutions of hybridoma media are applied and the plate is incubated 2 hours at room temp. The plate is washed several times as above and secondary antibody (1:5000 dilution of horseradish peroxidase (HRP) goat anti-mouse conjugate) is applied and the plate incubated one hour at room temp. After PBST washes, 100 μl/well TMB substrate is added and the plate incubated 30 minutes for color development. Reactions are stopped with 100 μl 0.18M sulfuric acid, and absorbance at 450 nm is determined. Conditioned media containing mAb at levels clearly above negative controls at dilutions of at least 1:1000 are used for mAb purification by FPLC.

Example 32. mAb Purification

Monoclonal antibody purification is done using affinity FPLC to capture and elute mAb's from hybridoma-conditioned media using protein G coupled to sepharose. Protein G binds to the Fc region of IgG from most species at or near physiological pH and ionic strength. Protein G Sepharose 4 Fast Flow resin may be used to isolate and purify classes, subclasses, and fragments of immunoglobulins from any biological fluid or cell culture media. The FPLC column is initially be equilibrated with binding buffer (20 mM $Na_2HPO_4$, pH 7.0). After loading of a 0.2 micron-filtered sample, unbound protein is monitored by UV and collected as a pooled sample. After additional buffer washes, IgG is eluted in 0.1 M glycine, pH 2.5 buffer, neutralized with buffer (1M Tris, pH 9.0), and stabilized with 150 mM NaCl. Columns are then be cleaned with additional elution and binding buffer washes for storage. Purified mAb are quantified using the BCA assay, and are stored frozen in 50% glycerol.

Example 33. Biochemical Assays

Western blot analysis. To determine the quality of the antibodies by western blot, 10% SDS denaturing gels are run with pure hSA (1 μg, 10 ng & 100 pg), human serum (2 μl serum, 1:100 dilution & 1:10,000 dilution), and pure hBuChE (1 μg, 10 ng & 100 pg). Gels are transferred onto polyvinyldifluoride (PVDF) membranes and blocked with 5% milk in PBST (phosphate buffer with 0.2% tween-20). The PVDF membranes are first blotted with primary antibodies (serum from pre-bleed, bleed #3, or final bleed) at 1:1000, 1:2000, or 1:5000 dilution in 1% milk in PBST (0.2% tween-20) for 1 hour at room temperature. Membranes are washed 3 times with PBST, five minutes each wash. The secondary antibody (goat anti-rabbit conjugated with horseradish peroxidase enzyme) is applied on the membranes with 1:10,000 dilution, in 1% milk in PBST (0.2% tween-20) for 1 hour at room temperature. Membranes are washed 3 times with PBST, five minutes each wash. SuperSignal West Pico Chemiluminescent Substrate (Pierce) was added to the membranes which react with horseradish peroxidase to produce a chemiluminescent product that can be visualized by exposing the blot to film. The control (unphosphonylated) peptide for hSA undergoes the conjugation to CP (KLH) and subsequent antibody procurement protocol. Polyclonal antibodies were isolated and assayed by Western Blot analysis.

Identification of OP modifications in proteins. An OP reactive reagent, e.g. 18-Rp,19-Rp,20-Rp,21-Rp,22-Rp,23-Rp,27-Rp,28-Rp or 18-Sp,19-Sp,20-Sp,21-Sp,22-Sp,23-Sp,27-Sp,28-Sp was dissolved in dimethylsulfoxide to make 100 mM solutions and used immediately. Human butyrylcholinesterase was purified from outdated human plasma by ion exchange chromatography at pH 4.0 followed by affinity chromatography on procainamide-Sepharose, and anion exchange at pH 7 on a Protein-Pak DEAE 8HR 1000 Å, 10×100 mm HPLC column (Waters/Millipore). The purified butyrylcholinesterase had an activity of 540 units/ml and a protein concentration of 0.75 mg/ml.

Inhibition of butyrylcholinesterase. A 0.25 ml aliquot of butyrylcholinesterase (0.19 mg=2.2 nmoles) in pH 7.4 phosphate buffered saline was treated with 1 μl of 100 mM OP analog at 21° C. for 17 h. The molar ratio of butyrylcholinesterase to nerve agent was 1:45.

Butyrylcholinesterase activity assay. The assay contained 1 mM butyrylthiocholine, 0.5 mM 5,5-dithiobis(2-nitrobenzoic acid) in 2 ml of 0.1 M potassium phosphate pH 7.0, at 25° C. and 1 μl of butyrylcholinesterase. The absorbance increase at 412 nm was recorded on a Gilford spectrophotometer. Activity was calculated from the extinction coefficient of 13,600 $M^{-1}cm^{-1}$. Units of activity are micromoles substrate hydrolyzed per min.

Digestion with trypsin. The nerve agent treated BChE was denatured in a boiling water bath for 10 min. The cooled solution received 2 μl of 1 M ammonium bicarbonate to raise the pH to about 8.3, and 10 μl of 0.4 μg/μl trypsin. Digestion was overnight at 37° C.

HPLC. Digests were centrifuged to remove a pellet and injected into a Phenomenex C18 column, 100×4.6 mm, on a Waters 625 LC system. Peptides were eluted with a 60 min gradient starting with 100% buffer A (0.1% trifluoroacetic acid in water), and ending with 60% buffer B (acetonitrile containing 0.09% trifluoroacetic acid) at a flow rate of 1 ml per min. One ml fractions were collected.

MALDI-TOF-TOF mass spectrometer. The digest before HPLC separation, as well as each HPLC fraction was analyzed in the MS mode on the MALDI-TOF-TOF 4800 mass spectrometer (Applied Biosystems, Foster City, Calif.). A 0.5 μl aliquot was spotted on an Opti-TOF 384 Well Insert (P/N 1016629, Applied Biosystems), dried, and overlaid with 0.5 μl of alpha-cyano-4-hydroxycinnamic acid (10 mg/ml in 50% acetonitrile, 0.1% trifluoroacetic acid). MS spectra were acquired using delayed extraction in reflector mode with a laser intensity of 3500 volts. Each spectrum was the sum of 500 laser shots. The instrument was calibrated with Glu-Fibrinopeptide standards. Spectra were saved to DATA EXPLORER™ where an output window listed the cluster area for each peak. Relative amounts of phosphonylated peptides before and after aging were calculated from cluster areas.

The peptide sequence and the identity of the modified amino acid were determined by fragmenting the parent ions in the MS/MS mode of the MALDI-TOF-TOF mass spectrometer. The y-ions and b-ions were assigned with the aid of the Proteomics Toolkit, a free online fragment ion calculator (db.systemsbiology.net).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A compound having the structure of Formula I:

OP-Peptide-Linker-CP (I)

or a salt thereof, wherein

OP represents the structure of

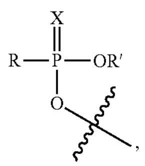

corresponding to that of a reactive organic phosphorous compound covalently modifying a tyrosine residue hydroxyl group of the peptide of Formula I, wherein P is in the $S_p$ or $R_p$ configuration, or a mixture thereof;

R is optionally substituted alkyl, optionally substituted cycloalkyl, optionally substituted aryl, optionally substituted heteroaryl, or optionally substituted amino;

R' is optionally substituted alkyl, optionally substituted cycloalkyl or optionally substituted aryl;

X is oxygen or sulfur;

Peptide is a partial sequence of amino acids of a serum albumin protein comprising a tyrosine residue hydroxyl group that is modified by the reactive organic phosphorous compound to have the OP structure, wherein the total number of amino acid residues in the sequence ranges from 7 to 41;

Linker is an amino acid residue or a residue from another bifunctional residue capable of covalently linking an OP-peptide to a CP of formula I; and CP is a carrier protein wherein the carrier protein is suitable for display of haptens for generation of antibodies selective and specific for an OP-peptide.

2. The compound of claim 1 wherein

R is methyl, ethyl, isopropyl, n-propyl, n-butyl, tert-butyl, cyclobutyl, methoxy, ethoxy, propoxy, mono alkylamino, or dialkylamino;

R' is methyl, ethyl, isopropyl, pinacolyl, or cyclohexyl; and

X is oxygen or sulfur.

3. The compound of claim 1 wherein the reactive organic phosphorous compound is a pesticide, a insecticide P═S to P═O metabolite, or a nerve gas agent.

4. The compound of claim 3, wherein the reactive organic phosphorous compound is a nerve gas agent.

5. The compound of claim 3, wherein the reactive organic phosphorous compound is a insecticide P═S to P═O metabolite.

6. The compound of claim 3, wherein the OP-peptide is a partial sequence of amino acids of human serum albumin protein comprising a tyrosine amino acid residue corresponding to tyrosine 411 of human serum albumin that is covalently modified by a insecticide P═S to P═O metabolite or a nerve gas agent.

7. The compound of claim 3, wherein the Linker is derived from or corresponds to aminocaproic acid.

8. The compound of claim 3, wherein CP is Keyhole Limpet Hemocyanin (KLH).

9. The compound of claim 3, wherein the peptide sequence of the OP-peptide is a partial peptide sequence of human serum albumin comprising a tyrosine amino acid residue corresponding to tyrosine 411 of human serum albumin that is modified by a insecticide P═S to P═O metabolite or a nerve gas agent;

Linker of the Formula I compound is derived from amino caproic acid; and

CP of the Formula I compound is Keyhole Limpet Hemocyanin (KLH).

* * * * *